US010397400B2

(12) United States Patent
Gupta et al.

(10) Patent No.: US 10,397,400 B2
(45) Date of Patent: Aug. 27, 2019

(54) ELECTRONIC CALL ASSISTANT BASED ON A CALLER-STATUS AND A CALLEE-STATUS

(71) Applicant: SONY CORPORATION, Tokyo (JP)

(72) Inventors: Rashmi Gupta, Bangalore (IN); Avneet Singh, Bangalore (IN)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/802,695

(22) Filed: Nov. 3, 2017

(65) Prior Publication Data
US 2019/0141190 A1 May 9, 2019

(51) Int. Cl.
H04M 3/493 (2006.01)
G10L 17/14 (2013.01)
A61B 5/00 (2006.01)
G10L 15/26 (2006.01)

(52) U.S. Cl.
CPC ............. *H04M 3/493* (2013.01); *G10L 17/14* (2013.01); *H04M 3/4936* (2013.01); *A61B 5/6802* (2013.01); *G10L 15/265* (2013.01); *H04M 2201/405* (2013.01)

(58) Field of Classification Search
CPC ....... H04W 4/14; H04W 76/14; H04W 40/20; H04M 1/72577; H04M 1/72552; H04M 1/64; H04M 1/7253; H04M 7/006; H04M 2207/18; H04M 2242/30; H04M 3/42382; H04M 1/6075; H04M 1/663; H04M 1/72572; H04M 2250/10; H04M 3/42263; H04M 1/67
USPC ...................... 379/207.02, 265.02, 52, 88.01
See application file for complete search history.

(56) References Cited

U.S. PATENT DOCUMENTS

| 8,054,961 B2* | 11/2011 | Skubnik ................ H04M 3/527 379/210.01 |
| 8,995,972 B1* | 3/2015 | Cronin .................... H04W 4/18 455/414.3 |
| 9,014,365 B1* | 4/2015 | Castiglione ......... H04M 3/5183 379/114.13 |
| 9,036,804 B2 | 5/2015 | Basu et al. |
| 9,554,356 B2 | 1/2017 | Dotan-Cohen et al. |

(Continued)

OTHER PUBLICATIONS

Whilston Gordon, "How to Turn Your Phone Into a Mind-Reading Personal Assistant", Sep. 10, 2012.

(Continued)

*Primary Examiner* — Akelaw Teshale
(74) *Attorney, Agent, or Firm* — Chip Law Group

(57) ABSTRACT

An electronic call assistant based on a callee-status and a caller-status, comprises one or more sensors, a memory, and a circuitry. The memory in the first electronic device may be configured to store a plurality of applications. The circuitry in the first electronic device is configured to determine an identity of a caller of a voice call received by the first electronic device from a second electronic device. A current callee-status of a callee associated with the first electronic device, is detected. The circuitry is configured to extract a text query from a speech signal in the received voice call. The circuitry is further configured to communicate a custom audio response to the second electronic device based on the extracted text query, the determined identity of the caller, current callee-status of the callee, and the level of access associated with the determined identity.

20 Claims, 10 Drawing Sheets

(56) References Cited

U.S. PATENT DOCUMENTS

| | | | |
|---|---|---|---|
| 2011/0107236 A1 | 5/2011 | Sambhar | |
| 2012/0208575 A1* | 8/2012 | Wilson | H04L 51/38 |
| | | | 455/466 |
| 2013/0157629 A1* | 6/2013 | Lee | H04W 4/16 |
| | | | 455/414.1 |
| 2014/0057610 A1* | 2/2014 | Olincy | H04W 4/16 |
| | | | 455/414.1 |
| 2014/0179227 A1* | 6/2014 | Nousiainen | H04W 84/18 |
| | | | 455/41.2 |
| 2014/0206321 A1* | 7/2014 | Mohapatra | H04W 4/12 |
| | | | 455/413 |
| 2014/0253666 A1* | 9/2014 | Ramachandran | H04W 4/12 |
| | | | 348/14.06 |
| 2015/0163341 A1* | 6/2015 | Skovron | H04M 1/72569 |
| | | | 455/418 |
| 2015/0271110 A1* | 9/2015 | Murray | H04L 51/02 |
| | | | 455/414.1 |

OTHER PUBLICATIONS

Laurane Goode, "Five Things You Didn't Know About Cortana, Microsoft's Virtual Assistant", Sep. 22, 2014.
Chris Hoffman, "16 Android Voice Actions to Make Android Your Own Personal Assistant", Mar. 6, 2013.

* cited by examiner

ELECTRONIC CALL ASSISTANT BASED ON A CALLER-STATUS AND A CALLEE-STATUS

CROSS-REFERENCE TO RELATED APPLICATIONS/INCORPORATION BY REFERENCE

None.

FIELD

Various embodiments of the disclosure relate to call assistant systems. More specifically, various embodiments of the disclosure relate to an electronic call assistant based on a caller-status and a callee-status.

BACKGROUND

Recent advancements in the field of telecommunications have extended the functionalities of various telecommunication devices, such as smartphones. In conventional systems, if a callee is not available to answer a particular call received at a smartphone, then a telecommunication server or an answering machine, may auto-answer the call and may play a pre-recorded audio to a caller. The telecommunication server or the answering machine may further record the audio of the caller during the duration of the call as a voice mail and may enable the callee to access the voice mail. However, the recorded voice mails often tend to be long and cluttered with irrelevant and superficial information. Therefore, the callee may find it cumbersome at a later point in time to derive useful information from the voice mails recorded for different callers. Further, the caller usually hear a static pre-recorded message from the conventional automatic call answering machines or call assistants regardless of the current-status of the caller.

Further limitations and disadvantages of conventional and traditional approaches will become apparent to one of skill in the art, through comparison of described systems with some aspects of the present disclosure, as set forth in the remainder of the present application and with reference to the drawings.

SUMMARY

An electronic call assistant and a method for operating the electronic call assistant based on a callee-status and a caller-status is substantially as shown in, and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

DETAILED DESCRIPTION

Figure 1:
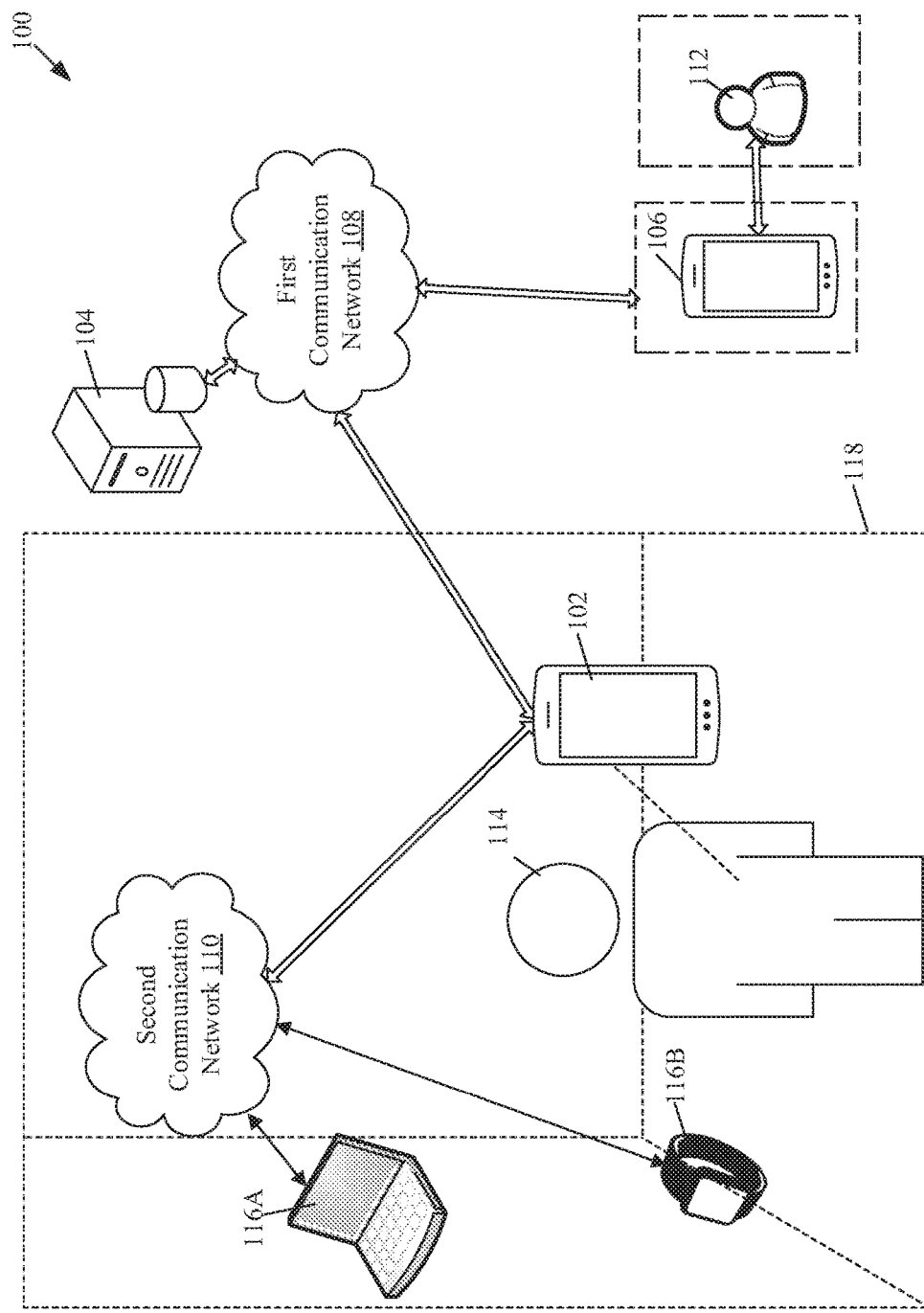
FIG. 1 illustrates an exemplary network environment for an electronic call assistant, in accordance with an embodiment of the disclosure.

The following described implementations may be found in the disclosed electronic call assistant based on a callee-status and a caller-status. Exemplary aspects of the disclosure may include a system that comprises a first electronic device. The first electronic device may comprise one or more sensors, a memory, and a circuitry. The memory in the first electronic device may be configured to store a plurality of applications. The circuitry in the first electronic device may be configured to determine an identity of a caller of a voice call received by the first electronic device from a second electronic device. The circuitry may be configured to acquire content from the plurality of applications and the one or more sensors of the first electronic device, based on the determined identity of the caller and a level of access associated with the determined identity. The circuitry may be further configured to detect a current status of a callee (callee-status) associated with the first electronic device based on the acquired content. The circuitry may be configured to extract a text query from a speech signal in the received voice call. The circuitry may be further configured to communicate a custom audio response to the second electronic device based on the extracted text query, the determined identity of the caller, the detected current callee-status of the callee, and the level of access associated with the determined identity.

In accordance with an embodiment, the current callee-status of the callee corresponds to an emotional status, a health status, a social media status, and a user availability status. The circuitry may be configured to establish a voice call session between the second electronic device of the caller and the first electronic device of the callee. The custom audio response may be communicated in the established voice call session. The circuitry may be further configured to capture at least an image or voice of the callee by the one or more sensors for the detection of the current callee-status of the callee. The circuitry may be further configured to predict a current caller-status of the caller associated with the second electronic device based on a voice stress level of the speech signal in the received voice call and the extracted text query. The circuitry may be further configured to compute an urgency level for the caller to communicate with the callee based on the predicted current caller-status of the caller.

In accordance with an embodiment, the circuitry may be further configured to modify the level of access associated with the determined identity based on the computed urgency level for the caller to communicate with the callee. In some embodiments, the circuitry may be further configured to detect a third electronic device currently used by the callee, and re-direct the received voice call from the first electronic device to the detected third electronic device of the callee, via a personal wireless network.

The circuitry may be configured to generate the custom audio response based on an analysis of the extracted text query, the determined identity of the caller, the detected current callee-status of the callee, and the level of access associated with the determined identity. The circuitry may be further configured to identify a relationship of the caller with respect to the callee based on the determined identity of the caller. In accordance with an embodiment, the circuitry may be further configured to determine a communication pattern and an emotional pattern of the caller based on historical data extracted from a plurality of voice calls previously received by the first electronic device from the second electronic device of the caller.

In accordance with an embodiment, the circuitry may be configured to generate a gist indicative of an intent of the received voice call. The gist may be generated based on the extracted text query, the level of access associated with the determined identity of the caller, and learned information from a plurality of voice calls previously received by the first electronic device, from the same identity of the caller. The circuitry may be further configured to control display of a custom notification at the first electronic device. The custom notification may comprise a missed call indication from the caller along with and the gist indicative of the intent of the received voice call. The circuitry may be further configured to communicate the custom notification from the first electronic device to a third electronic device used by the callee, based on an absence of the callee in a defined physical area in which the first electronic device is located.

FIG. 1 illustrates an exemplary network environment for an electronic call assistant based on a callee-status and a caller-status, in accordance with an embodiment of the disclosure. With reference to FIG. 1, there is shown an exemplary environment 100. The exemplary network environment 100 may include a first electronic device 102, a server 104, a second electronic device 106, a first communication network 108, and a second communication network 110. There is also shown a callee 114 associated with the first electronic device 102 and a caller 112 associated with the second electronic device 106. The first electronic device 102, the server 104, and the second electronic device 106 may be communicatively coupled to each other via the first communication network 108. There is also shown a third electronic device 116A and a fourth electronic device 116B that are communicatively coupled to the first electronic device 102 via the second communication network 110 in a defined physical area 118, for example, a home space, an office area, and the like.

The first electronic device 102 may comprise suitable logic, circuitry, interfaces, and or code that may be configured to determine an identity of a caller, such as the caller 112, of a voice call received by the first electronic device 102 from the second electronic device 106. The first electronic device 102 associated with the callee 114 may comprise one or more sensors to capture one or more data items associated with the callee 114. For example, the one or more sensors may comprise an image-capture device to capture an image of the callee 114, an audio-capture device to capture voice of the callee 114, and a location sensor (such as Global Positioning System (GPS) sensor) to detect a location of the first electronic device 102. Examples of the image-capture device may include, but are not limited to an integrated camera, a webcam, a fish eye camera, and a 360 degree view camera. Examples of the audio-capture devices may include, but are not limited to a lapel microphone, an integrated microphone, or a wireless microphone.

The first electronic device 102 may be configured to acquire content from a plurality of applications, for example, social network application, calendar application, wearable device-related applications, and the like, installed in the first electronic device 102 and the one or more sensors of the first electronic device 102. The acquisition of content may be done in accordance with the determined identity of the caller and a level of access associated with the determined identity. Examples of the first electronic device 102 may include, but are not limited to a smartphone, an intelligent answering machine, an electronic call assistant device, a personal assistant device, a tablet computer, a telecommunication device, a smart watch, a laptop, or other consumer electronic device.

The server 104 may comprise suitable logic, circuitry, interfaces, and/or code that may be configured to communicate with the first electronic device 102 and the second electronic device 106 via the first communication network 108. In some embodiments, certain operations, such as voice recognition and natural language processing (NLP) may be done at the server 104 in conjunction with the first electronic device 102. Examples of the server 104 may include, but are not limited to, an application server, a cloud server, a web server, a database server, a file server, a mainframe server, or a combination thereof.

The second electronic device 106 may comprise suitable logic, circuitry, interfaces, and or code that may be configured to establish a voice call session with the first electronic device 102. The second electronic device 106 of the caller 112 may output a custom audio response received from the first electronic device 102 in case the call may not be answered by the callee 114. For example, a different custom audio response may be generated in real time or near-real time for different callers based on current callee-status of the callee 114. Examples of the second electronic device 106 may include, but are not limited to a smartphone, a telephone, a personal assistant device, a tablet computer, a telecommunication device, a smart watch, a laptop, or an electronic call assistant device.

The first communication network 108 may include one or more mediums through which the second electronic device 106 may communicate with the first electronic device 102 to establish a voice call or other communication. The first communication network 108 may also include a medium through which the first electronic device 102 may communicate with the server 104. Examples of the first communication network 108 may include, but are not limited to the Internet, a public switched telephone network (PSTN), a third generation (3G), 4G, or 5G mobile network, a radio communication network, a cloud network, or a Wireless Fidelity (Wi-Fi) network. Various devices in the exemplary environment 100 may be configured to connect to the first communication network 108, in accordance with various wired and wireless communication protocols. Examples of such wired and wireless communication protocols may include, but are not limited to, at least one of a Transmission Control Protocol and Internet Protocol (TCP/IP), a Bluetooth protocol, User Datagram Protocol (UDP), Hypertext Transfer Protocol (HTTP), File Transfer Protocol (FTP), EDGE, IEEE 802.11, IEEE 802.11b, IEEE 802.11g, IEEE 802.11n, IEEE 802.11x and/or any other IEEE 802.11 protocol, multi-hop communication, wireless access point (AP), device to device communication, cellular communication protocols, or a combination or variants thereof.

The second communication network 110 may include one or more mediums through which the first electronic device 102 may communicate with other personal devices, such as the third electronic device 116A and the fourth electronic device 116B, in the defined physical area 118. The second communication network 110 may refer to an Internet-of-Things (IoT) based network, a personal wireless network, a smart home network, the Internet, a Local Area Network (LAN), or a personal wireless network (PAN). Various devices in the exemplary environment 100 may be configured to connect to the second communication network 110, in accordance with various wired and wireless communication protocols.

Each of the third electronic device 116A and the fourth electronic device 116B may comprise suitable logic, circuitry, interfaces, and or code that may be configured to receive a custom notification from the first electronic device 102. Each of the third electronic device 116A and the fourth electronic device 116B may output the custom notification received from the first electronic device 102 in case the call is not answered by the callee 114. For example, a different custom notification may be generated in real time or near-real time for different callers based on current callee-status of the callee 114. Examples of the third electronic device 116A and the fourth electronic device 116B may include, but are not limited to a wearable device (such as a smart watch a smart band, a smart glass), an IoT-enabled device, such as an IoT enabled music system, an IoT enabled microwave, an IoT enabled washing machine, an IoT enabled refrigerator, an IoT enabled coffee machine, an IoT enabled printer or photo-copier, a tablet computer, a laptop, another smart-phone, or a personal computing device.

The defined physical area 118 may refer to an area situated within a building, or a certain specified range of indoor or outdoor area surrounding a first user, such as the callee 114, at the time when a call is received from the caller 112. For example, the defined physical area 118 may be an office area, a home area, an interior of a vehicle, or a recreational area used by the user, such as the callee 114, at the time of the call. Various personal devices, such as the first electronic device 102, the third electronic device 116A, and the fourth electronic device 116B, of the first user (such as the callee 114) may be present in the defined physical area 118.

In operation, the first electronic device 102 may be configured to receive a plurality of voice calls from a plurality of different users (such as the caller 112 and other callers) via the first communication network 108. The first electronic device 102 may be configured to record and communicate the plurality of voice calls to the server 104. In some embodiments, the recorded data may not be accessible to the first electronic device 102 for privacy, and may be used exclusively for processing purpose based on user-defined setting. The server 104 may be configured to process the plurality of voice calls to determine a communication pattern of each user of the plurality of different users. For example, the first electronic device 102 may receive a plurality of voice calls over a period of time from the same user (such as the caller 112). The first electronic device 102 may be configured to receive speech signals associated with the caller 112 during each voice call session of the plurality of voice calls. In some embodiments, the first electronic device 102 may be configured to process the speech signals to extract textual information from the speech signals. In some embodiments, the first electronic device 102 may be configured to communicate the voice data that includes the speech signals to the server 104 for extraction of textual information, and further processing. The textual information may indicate information communicated by the caller 112 in each voice call session of the plurality of voice calls from the caller 112. The extracted textual information may be stored in the first electronic device 102 (or the server 104) as historical data.

In one example, the first electronic device 102 (or the server 104) may be configured to analyze the plurality of voice calls received from a same user, such as the caller 112 and the extracted textual information to learn a communication pattern and an intent of each call to the callee 114 over a period of time. For example, the caller 112 may say "I am Robert, and I am an Engineer" in a voice call session. The first electronic device 102 (or the server 104) may extract the text "I am Robert" and "I am an Engineer" from the voice call session. The first electronic device 102 may be further configured to identify the caller 112 as "Robert" and may be further configured to identify the caller 112 to be an engineer. The first electronic device 102 may receive a caller identity of the caller 112 (i.e. a phone number of same user) from the first communication network 108. The first electronic device 102 may be configured to store the received caller identity in association with the textual information extracted from the plurality of voice calls, as the historical data extracted from the plurality of the voice calls.

The first electronic device 102 may be further configured to analyze the speech signals in each of voice call sessions, to determine a communication pattern associated with the caller 112. The communication pattern may include a pattern related to context or intent of a call. The communication pattern may comprise information with respect to accent, speech mannerism, speech impediments, languages used, age, eloquence, articulation capability, pitch, and tone associated with the caller 112. The determined communication pattern may further comprise a baseline pitch, a baseline speech rate, and a baseline behavior determined for the caller 112. The communication pattern may further comprise information associated with specific euphemisms used by the caller 112. The communication patterns may comprise information indicative of whether the caller 112 conveys relevant data in a concise manner in a voice call or whether the caller 112 conveys a mixture of the relevant and irrelevant information. The first electronic device 102 may determine the communication pattern based on the analysis of the speech signals as well as based on the historical data extracted from the plurality of voice calls received from the caller 112 over a period of time.

The first electronic device 102 may further determine an emotional pattern associated with the caller 112, based on the analysis of the speech signals in the plurality of established voice call sessions. The emotional patterns may comprise information with regards to temperament of the caller 112. The first electronic device 102 may classify the caller 112 as a user of one of a jovial temperament, patient temperament, short temperament, excited temperament, or neutral temperament based on the emotional pattern determined for the caller 112. The emotional pattern may further comprise types of verbal cues, variation in pitch, and variation in tone of the caller 112 which may be deemed useful for the first electronic device 102 to identify moods of the caller 112 in real time or near real time for a later voice call. Examples of the moods of the caller 112 may comprise a happy mood, a sad mood, an excited mood, or a neutral mood. Further, the emotional pattern may further comprise information regarding types of verbal cues and verbal strains in speech of the caller 112, which may indicate stress levels of the caller 112.

In some embodiments, the second electronic device 106 may be further configured to analyze speech signals received from the caller 112 during each established voice call session with the first electronic device 102 to determine an emotional state of the caller 112. Examples of the emotional state of the caller 112 may include, but are not limited to a jovial state, a gloomy state, an agitated state, an excited state, and/or a neutral state. The second electronic device 106 may further comprise a location sensor, a camera, a health sensor and an audio sensor. In some embodiments, a prompt may be output (a visual or audio output) on the second electronic device 106 to seek a confirmation from the caller 112 to the use of sensors for emotional state recognition of the caller 112. In cases where the caller 112 confirms or agrees to allow emotional state recognition of the caller 112, the various sensors of the second electronic device 106 may be utilized to determine the emotional state of the caller 112. For example, the camera may capture one or more images of surroundings of the second electronic device 106. The audio sensor may be configured to capture one or more audio streams from surroundings of the second electronic device 106. The health sensor (such as a heart rate monitor) may be configured to detect a stress level of the caller 112. The location sensor (such as a GPS sensor) may detect a location of the caller 112. Thus, the second electronic device 106 may be configured to analyze the emotional status of the caller 112 based on the input from various sensors, such as the captured images, the captured audio streams, and also the detected stress levels to determine a current caller-status of the caller 112.

The current caller-status of the caller 112 may be temporally stored as metadata. The metatada then may be encoded and transmitted to the first electronic device 102 at audio frequencies that is beyond the human auditory range. For example, the second electronic device 106 may be configured to generate a caller-status-based audio signal based on the determined current-caller-status (e.g. the metadata by encoding) of the caller 112. In some embodiments, the caller-status-based audio signal may be generated at a frequency which may not be within human auditory range. For example, the second electronic device 106 may be configured to generate the caller-status-based audio signal at frequency which may be lesser than 20 hertz or higher than 20 Kilohertz. Typically, human auditory range is between 20 to 20000 hertz. Thus, the caller-status based audio signal at frequency lesser than 20 hertz or higher than 20000 hertz may be inaudible to humans. The second electronic device 106 may transmit the caller-status of the caller 112 to the first electronic device 102 via voice channels of the established call instead of data channels. Therefore, the second electronic device 106 may transmit the caller-status without the use of internet. The first electronic device 102 may then extract (or decode the encoded metadata transmitted as the caller-status-based audio signal which is beyond human auditory range) the caller-status-based audio signal from voice channels of the plurality of established voice call sessions. The first electronic device 102 may be configured to analyze the extracted caller-status based audio signals to acquire a caller-status of the caller 112 from the second electronic device 106. The first electronic device 102 may be configured to determine the emotional pattern of the caller 112 based on the caller-status of the caller 112.

In accordance with an embodiment, the first electronic device 102 may store the determined communication pattern and the emotional pattern associated with the caller 112 in a database. Similar to the caller 112, communication pattern and emotional pattern may be determined for each user of the plurality of different users. In some embodiments, the communication pattern and emotional pattern may be determined for selected users based on user-defined criteria, for example, the users who are in the contact list of the first electronic device 102, user-selected user groups, such as family members, unknown phone numbers, or for all voice calls received at the first electronic device 102. In some embodiments, the communication pattern and the emotional pattern of each user may be determined and stored at the server 104.

In accordance with an embodiment, the first electronic device 102 or the server 104 may be configured to store determined communication patterns and determined emotional patterns of the plurality of different users in association with corresponding identity of each user (i.e. each caller). An example is shown in TABLE 1.

TABLE 1

Exemplary communication patterns and the emotional patterns.

| USER_NAME | USER_IDENTITY | COMMUNICATION_PATTERN | EMOTIONAL_PATTERN |
|---|---|---|---|
| Paul - | 015554787 | Fast speaker, New York Accent | Jovial Temperament |
| Gary | 0645487448 | Slow Speaker, Cockney Accent | Patient Temperament |
| Ryan | 0151454555 | Loud Speaker, Boston Accent | Neutral Temperament |
| Giovanna | 015548451 | Fast Speaker, Italian Accent | Short Temperament |

In accordance with an embodiment, the first electronic device 102 may be configured to store a plurality of applications. The plurality of applications may comprise, for example, social media applications, social media messenger applications, email client applications, Short Message Service (SMS) client applications, reminder applications, web browser application, wearable-device related applications, user activity tracking applications (such as lifelog application), and calendar applications. The first electronic device 102 may be configured to receive application-based data from the plurality of applications. Examples of the application-based data include, but are not limited to messages (e.g. SMS messages) received by the first electronic device 102, emails associated with the callee 114, social media posts associated with the callee 114, lifelog entries, calendar entries, and reminders intended for the callee 114. The first electronic device 102 may be further configured to extract user information associated with the caller 112, and other users from the application-based data based on the identity of the caller 112. Examples of the extracted user information comprises caller 112 a relationship of the caller 112 with respect to the callee 114, and specific calendar entries associated with the callee 114 and the caller 112.

In accordance with an embodiment, all the above, such as communication pattern, emotional pattern, and the application-based data, may be later utilized by the first electronic device 102 as historical data or learned information when a new call is received. For example, in the case where the callee 114 is unavailable to answer the call, a call assistant application installed in the first electronic device 102 may be configured to auto-answer the new call received. The call assistant application may be further configured to extract a textual query based on analysis of one or more speech signals received via a voice call session associated with the new call received. Further, the call assistant application may be configured to use the historical data (such as a communication pattern of the caller 112, an emotional pattern of the caller 112, and the application based data) to generate a gist of the extracted text query.

Figure 2:
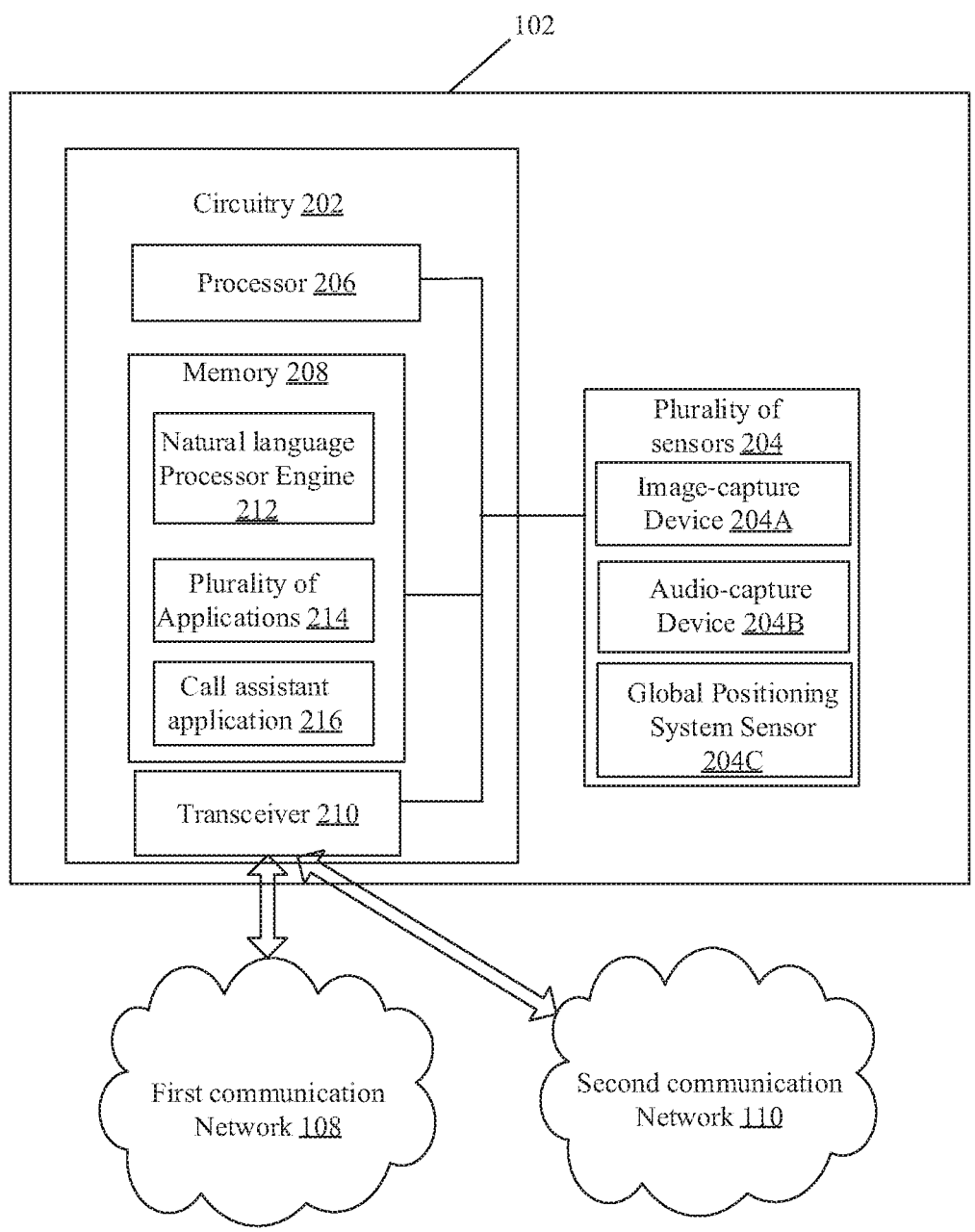
FIG. 2 is a block diagram that illustrates an exemplary electronic device for implementation of an electronic call assistant, in accordance with an embodiment of the disclosure.

FIG. 2 is a block diagram that illustrates an exemplary electronic device for implementing an electronic call assistant, in accordance with an embodiment of the disclosure. FIG. 2 is explained in conjunction with elements from FIG. 1. With reference to FIG. 2, there is shown a first electronic device 102. The first electronic device 102 may comprise a circuitry 202 and a plurality of sensors 204. The plurality of sensors 204 may comprise an image-capture device 204A, an audio-capture device 204B, a global positioning system sensor 204C, and other type of sensors (such as heart rate sensors and the like). The circuitry 202 may comprise a processor 206, a memory 208, and a transceiver 210. There is also shown the first communication network 108 and the second communication network 110. The memory 208 may comprise a natural language processor engine 212, a plurality of applications 214, and a call assistant application 216.

In accordance with an embodiment, the first electronic device 102 may be communicatively coupled to one or more other electronic devices or server 104, through the first communication network 108, and/or the second communication network 110, via the transceiver 210. In accordance with an embodiment, the circuitry 202, comprising the processor 206, may be communicatively coupled to, the plurality of sensors 204, the memory 208 and/or the transceiver 210. In other embodiments, the circuitry 202 may be communicatively coupled with the the plurality of sensors 204, the memory 208 and/or the transceiver 210 via a system bus or various software interfaces such as application program interfaces and cross-program interfaces. In accordance with an embodiment, the first electronic device 102 may be an electronic call assistant that may include one or more logic, circuitry, and/or code configured to provision an electronic call assistant functionality.

The plurality of sensors 204 may comprise suitable logic, circuitry, interfaces, and/or code that may be configured to sense one or more parameters and communicate the sensed one or more parameters to the circuitry 202. The plurality of sensors 204 may comprise the image-capture device 204A, which may be configured to capture images from vicinity of the first electronic device 102. In certain scenarios, the image-capture device 204A may comprise suitable logic, circuitry, and/or interfaces that may be configured to capture images of callee's face. The plurality of sensors 204 may further comprise the audio-capture device 204B, which may comprise suitable logic, circuitry, and/or interfaces that may be configured to capture audio streams from the vicinity of the first electronic device 102. The plurality of sensors 204 may further comprise a GPS sensor 204C which may comprise suitable logic, circuitry, and/or interfaces that may be configured to determine location of the first electronic device 102. Examples of the image-capture device 204A may include a integrated camera, a web cam, a wide angle camera, a fish eye camera, and/or a 360 degree camera. Examples of the audio-capture device 204B may include a shotgun microphone, a lapel microphone, a handheld microphone, a smartphone, a wireless microphone, and/or an omnidirectional microphone.

The processor 206 may comprise suitable logic, circuit components, interfaces, and/or code that may be configured to execute a set of instructions stored in the memory 208. The processor 206 may be configured to execute a set of instructions by use of the natural language processor engine 212, the plurality of applications 214, and the call assistant application 216 installed in the memory 208. Examples of the circuitry 202 may include, but are not limited to an X86-based processor, a Reduced Instruction Set Computing (RISC) processor, an Application-Specific Integrated Circuit (ASIC) processor, a Complex Instruction Set Computing (CISC) processor, a microcontroller, a microprocessor, and/or other processing circuitry or control circuits.

The memory 208 may comprise suitable logic, circuitry, and/or interfaces that may be configured to store a set of instructions executable by the circuitry 202. Examples of implementation of the memory 208 may include, but are not limited to Random Access Memory (RAM), Read Only Memory (ROM), Hard Disk Drive (HDD), a solid state drive (SSD), and/or a Secure Digital (SD) card. The memory 208 may be further configured to store the application-based data, the plurality of call response templates, the communication patterns of the plurality of users, the emotional pattern of the plurality of users, and/or the historical data or learned information extracted from the plurality of voice calls.

The memory 208 may further comprise suitable logic, circuitry, and/or interfaces that may be correspond to the natural language processor engine 212, executable by the circuitry 202. The natural language processor engine 212 may be configured to convert voice to text and extract text queries from the plurality of voice call sessions associated with the plurality of voice calls received at the first electronic device 102. The memory 208 may further comprise the plurality of applications 214. The plurality of applications 214 may comprise a social media application, a social media messenger application, an email client application, an SMS client application, a reminder application, a web browser application, a user activity tracker application (such as lifelog application), and a calendar based application, as discussed in FIG. 1.

The call assistant application 216 may be installed in the memory 208, which may be configured to assist the callee 114 during a course of one or more voice calls received at the first electronic device 102. In accordance with an embodiment, the call assistant application 216 may include software component installed in the memory 208. In accordance with an embodiment, the functionalities of the call assistant application 216 may be implemented as a part of the circuitry 202. Examples of implementation of the memory 208 may include, but are not limited to, Random Access Memory (RAM), Read Only Memory (ROM), Hard Disk Drive (HDD), a Secure Digital (SD) card, and/or other Solid State Device (SSD). In accordance with an embodiment, the call assistant application 216 may be installed from remote systems, such as a cloud server. In some embodiments, the first electronic device 102 (i.e. a callee device) and the second electronic device 106 (i.e. a caller device) may be able to run the or operate the call assistant application 216 stored remotely in the server 116. In some embodiments, the call assistant application 216 may be implementable as an application program running in a thin-client computer terminal which may be associated with the server 116, which may be a cloud server. In some embodiments, the call assistant application 216 may be hosted by a thin-client computer terminal which may be associated with servers of a mobile service provider.

The transceiver 210 may comprise suitable logic, circuitry, interfaces, and/or code that may be configured to communicate with other electronic devices, via the first communication network 108 and the second communication network 110. The transceiver 210 may implement known technologies to support wireless communication. The transceiver 210 may include, but are not limited to an antenna, a radio frequency (RF) transceiver, one or more amplifiers, a tuner, one or more oscillators, a digital signal processor, a coder-decoder (CODEC) chipset, a subscriber identity module (SIM) card, and/or a local buffer.

The transceiver 210 may communicate via offline and online wireless communication with networks, such as the Internet, an Intranet, and/or a wireless network, such as a cellular telephone network, a wireless local area network (WLAN), personal area network, and/or a metropolitan area network (MAN). The wireless communication may use any of a plurality of communication standards, protocols and technologies, such as Global System for Mobile Communications (GSM), Enhanced Data GSM Environment (EDGE), wideband code division multiple access (W-CDMA), code division multiple access (CDMA), LTE, time division multiple access (TDMA), Bluetooth, Wireless Fidelity (Wi-Fi) (such as IEEE 802.11, IEEE 802.11b, IEEE 802.11g, IEEE 802.11n, and/or any other IEEE 802.11 protocol), voice over Internet Protocol (VoIP), Wi-MAX, Internet-of-Things (IoT) technology, Machine-Type-Communication (MTC) technology, a protocol for email, instant messaging, and/or Short Message Service (SMS).

In operation, the circuitry 202 in the first electronic device 102 (associated with the callee 114) may be configured to receive a voice call from the second electronic device 106 (associated with the caller 112) by use of the transceiver 210. The circuitry 202 may be configured to receive the voice call via the first communication network 108. Examples of the voice calls include a voice over Internet Protocol (VoIP) call, cellular network-based calls or Public Switched Telecommunication Network (PSTN) based calls, application to application calls, and further, gateway calls between a PSTN network and a VoIP based network (such as telephone calls occurring between a first smartphone registered to a second generation (3G) telecommunication network and a second smartphone registered to a fourth generational (4G) or 5G telecommunication network). However, in some cases, the callee 114 may not be available to receive the voice call. The call assistant application 216 stored in the memory 208 may be configured to auto-answer the received voice call and establish a voice call session for the received call, in the case the callee 114 is unavailable to attend the voice call at the first electronic device 102.

In accordance with an embodiment, the circuitry 202 may be configured to determine an identity of the caller 112 associated with the received voice call. The identity of the caller 112 may be at least one of a username, a phone number, and an email address. In certain scenarios, to determine the identity of the caller 112, the circuitry 202 may be configured to extract a phone number from the received call, via a caller identity feature associated with the received voice call. In cases where the phone number is an unknown number (not in contact list of the first electronic device 102), the circuitry 202 may be configured to compare the extracted phone number with one or more phone numbers in the application-based data (for example, by use of the social network application). If a first phone number in the application-based data matches with the extracted phone number, then the first electronic device 102 determines a name associated with the first phone number to be the identity of the caller 112.

In accordance with an embodiment, the circuitry 202 may be configured to check whether a level of access is associated with the determined identity of the caller 112. In one example, a user, such as the callee 114 may assign a particular level of access to different users already in contact list of the callee 114. In another example, the callee 114 may assign a first level of access to family members, a second level of access to friends, a third level of access to office colleagues, and a fourth level of access to other known and unknown users, by use of the call assistant application 216. In some embodiments, where an association of the determined identity of the caller 112 with a particular level of access, may not be established, the circuitry 202 may be configured to analyze certain defined applications of the plurality of applications 214, such as social network application, by use of the processor 206, to determine a relationship of the caller 112 with respect to the callee 114. The circuitry 202 may be configured to then dynamically assign a level of access to the determined identity, based on the determined relationship of the caller 112 with respect to the callee 114.

The circuitry 202 may be configured to analyze application-based data of certain specified applications in the plurality of applications 214, to determine the identity and associated relationship of the caller 112. In certain scenarios, the application-based data may comprise emails associated with the callee 114. For example, if the determined identity of the caller 112 is a name, "Robert", and if a first email from the callee 114 has a reference "Hello Uncle Robert,", then the first electronic device 102 may analyze the first email and identify the determined identity of the caller 112 to be an uncle of the caller 112. In certain scenarios, even though the caller 112 may be a person unknown to the callee 114, the caller 112 may be associated with the callee 114 for a particular purpose. For example, the caller 112 may be a delivery boy assigned to deliver a parcel to the caller 112 on a particular day. If the application-based data comprises an SMS with a text "Robert (contact no. 9999999999) shall deliver the parcel to you today", then the first electronic device 102 may be configured to determine identity of the caller 112 based on a match of the unknown phone number with the contact no. in the SMS, to be that of the delivery boy.

The level of access of the caller 112 indicates amount of information of the callee 114 (extracted from the application-based data), which can be safely divulged to the caller 112, without breach of the callee's privacy. In certain scenarios, the level of access may comprise a first level of access apt for a family member, a second level of access apt for a close friend, a third level of access apt for a professional colleague, and a fourth level of access apt for an unknown person. For example, if the caller 112 is determined by the circuitry 202 to be an uncle of the callee 114, then the caller 112 may be assigned the first level of access. However, if the caller 112 is determined by the first electronic device 102 to be an unknown person then the caller 112 may be assigned with the fourth level of access. In certain scenarios, the circuitry 202 may store information associated with the level of access assigned to the plurality of different users in the memory 208, based on determined relationship associated with each user of the plurality of different users. For example, the circuitry 202 may be configured to tabulate information associated with the levels of access in a table, as is shown in TABLE 2.

TABLE 2

User identity and corresponding levels of access

| User | User_Identity | Relationship | Level_of_access |
|---|---|---|---|
| Paul (Callee 114) | Phone_number_1 | Family member | First level |
| Gary (caller 112) | Phone_number_2 | Friend | Second level |
| Ryan | Phone_number_3 | Delivery boy | Fourth level |
| Giovanna | Phone_number_4 | Wife | First Level |

In accordance with an embodiment, the first electronic device 102 may be configured to analyze the application-based data to generate a contextual information associated with the caller 112. The contextual information may comprise information associated with the caller 112, such as a profession of the caller 112, the relationship of the caller 112 with respect to the callee 114, one or more tasks with which the caller 112 is engaged. The first electronic device 102 may be configured to modify the level of access assigned to the caller 112 based on the generated contextual information.

In one example, the first electronic device 102 of the callee 114 may receive a call from an known number, for example, from a friend of the callee 114. A calendar application of the plurality of applications 214 may be previously stored in the memory 208. A data item (such as a calendar entry in the calendar application) may indicate that the callee 114 may be in office during a defined time interval on certain days, for example, between "9 am" to "7 pm" on certain days. In cases where the call may be received during such defined time interval (i.e. a time interval during which the callee 114 may be in office), the callee 114 may not be interested in attending the call. In such cases, the first electronic device 102 may be configured to modify the level of access of the caller 112 from the second level of access to the third level of access. In other cases where the call is received outside the defined time interval (i.e. when the callee 114 is not in office), the callee 114 may be interested in answering the call. In such cases, the first electronic device 102 may be configured to dynamically modify the level of access of the caller 112 from the second level of access to the first level of access.

In another example, the first electronic device 102 of the callee 114 may receive a call from an unknown number, for example, a delivery boy. The callee 114 may be busy or away from the first electronic device 102, and thereby may not be available to attend the received voice call. The call assistant application 216 in the first electronic device 102, may establish a call session, where an intent of the caller, such as the delivery boy in this case, may be determined. The intent in this case may be determined as a delivery boy that intends to deliver a parcel at the home address of the callee 114 based on the analysis of speech signals in the call session. In accordance with an embodiment, intent of the call from the caller 112, for example, the delivery boy, may be determined based on analysis of application-based data by the processor 206. A fourth level of access may be initially assigned to the caller, such as the delivery boy, based on the detected identity of caller 112 determined as "unknown". However, based on analysis of application-based data by the processor 206, by use of the call assistant application 216, the circuitry 202 may dynamically change the level of access.

In one example, the first electronic device 102 may have previously received (and stored in the memory 208), an email or a message (SMS) from a courier service provider that a delivery of a parcel is scheduled for a certain day or time by <name of delivery boy> and <phone number of the delivery boy>). Thus, when the call is received, the first electronic device 102 may compare the received number (phone number of delivery boy) with the contact no. in various application-based data, such as a phone contact list, an email application, a messaging application, and the like, to find the identity of the received number. Based on the analysis of the received email, a match of the received number and the contact number, may be established. Thus, the first electronic device 102 may analyze the email to generate the contextual information, that the unknown caller is "Ralph Emerson" who is a delivery boy having a parcel meant for the callee 114.

In the case where an urgency is detected, the first electronic device 102 may be configured to modify the level of access of the unknown caller from the fourth level of access to the third level of access. For example, other applications, such as calendar application, social network applications, which are accessible exclusively for the third level of access, may then be analyzed. A customized voice message may be output for the caller, for example, the delivery boy, that the callee 114 (receiver of parcel) is busy in meeting, and may be contacted with after 30 minutes. Similarly, in some embodiments, based on the detected intent and urgency, the call may be forwarded from the circuitry 202 to the fourth electronic device 116B via the transceiver 210 and the second communication network 110. The call may be forwarded when a location of the callee 114 of the first electronic device 102 is detected away from circuitry 202 but in close proximity to the fourth electronic device 116B.

In accordance with an embodiment, each of the plurality of applications 214 stored in the memory 208 may be tagged with a defined or a particular privacy level by use of the call assistant application 216 installed in the memory 208. The circuitry 202 may be configured to allow or deny access to the extracted application-based data to different users based on levels of access assigned to the different users and privacy levels associated with the plurality of applications 214. The privacy levels may be one of a first privacy level, a second privacy level, a third privacy level, and a fourth privacy level. The privacy level may be indicative of a user's confirmation (or agreement) that a particular application or data items of the particular application may be analyzed without breach of privacy of the callee 114.

The circuitry 202 may be configured to allow or deny access to content associated with different users based on the levels of access assigned to the different users and/or the privacy levels. For example, if the caller 112 has a third level of access, and exemplary data items belong to a social network application that has the second privacy level, then the circuitry 202 may prevent the caller 112 from accessing the exemplary data items, because the caller 112 lacks at least the second level of access needed to access the exemplary data items.

In accordance with an embodiment, the circuitry 202 may be configured to acquire content associated with the callee 114, from the plurality of applications 214 stored in the memory 208 and the one or more sensors in the plurality of sensors 204. Examples of the content acquired from the plurality of applications 214, may include but is not limited to data items such as email addresses, phone numbers, office address, social media status, home address, user activity information, and daily schedule associated with the callee 114. Examples of the content acquired by the circuitry 202 from the one or more sensors may include, but is not limited to images, audio streams, video, and location coordinates associated with the callee 114, captured by the one or more sensors.

In accordance with an embodiment, the circuitry 202 may be configured to acquire content based on the determined identity of the caller 112 and the assigned level of access associated with the determined identity of the caller 112. In some embodiments, the first electronic device 102 may be configured to acquire content based on the determined identity of the caller 112, a combination of the tagged privacy level for an application or data items, and the assigned level of access associated with the determined identity of the caller 112. The content may be acquired from the plurality of applications 214, the plurality of sensors 204, or a combination thereof. Further, the circuitry 202 may be configured to analyze the acquired content to detect a current callee-status of the callee 114.

The current callee-status may comprise several aspects about the callee 114 such as information associated with a health status of the callee 114, an emotional state of the callee 114, a social media status of the callee 114, information associated with one or more tasks that the callee 114 may be engaged in, a user-availability status of the callee 114, or a combination thereof. The health status of the callee 114 may indicate whether the callee 114 is healthy, tired, active, inactive, or suffering from a psychological or physiological ailment. Examples of the emotional state of the callee 114 may include, but are not limited to a jovial state, a gloomy state, an agitated state, an excited state, and/or a neutral state. The social media status of the callee 114 may be associated with one or more posts shared by the callee 114 in a social media platform by use of a social network application. Examples of the user-availability status may include, but are not limited to an "Available", "unavailable", "In a meeting", "Busy", or "In Gym" status.

In one example, the caller 112 may be associated with a second level of access that includes access to certain application. In such a case, the circuitry 202 may acquire content comprising the one or more posts from the social media platform as the caller 112 has the second level of access. Further, the one or more posts may indicate that the callee 114 may be watching a movie. The circuitry 202 may be configured to analyze the acquired content (i.e., the one or more posts) to determine that the user availability status of the callee 114 to be "Busy" or a custom status of "watching a movie".

In other scenarios, the circuitry 202 may be configured to acquire content, from the plurality of sensors 204. For example, the circuitry 202 may be configured to capture an image of the face of the callee 114 from the image-capture device 204A, at the time of receipt of the voice call. The circuitry 202 may be configured to analyze the image of the callee's face to determine a current emotional state of the callee 114. The circuitry 202 may also determine the health state of the callee 114, based on the analysis of the captured image of the callee's face. The circuitry 202 may be further configured to extract biometric data associated with the callee, from the captured image of the callee's face.

The circuitry 202 may be further configured to capture an audio stream from an area in the vicinity of the callee 114, by use of the audio-capture device 204B of the plurality of sensors 204. The circuitry 202 may be configured to analyze the captured audio stream with the processor 206, to determine the emotional state of the callee 114. For example, in certain scenarios, the first electronic device 102 may be located in a close proximity of the callee 114, and the callee 114 may be engaged in conversation with one or more other people in the area in the vicinity of the callee 114. In such scenarios, the captured audio stream may comprise one or more speech signals associated with the callee 114 and the one or more other people near the callee 114. The first electronic device 102 may be configured to analyze the audio stream to derive the one or more speech signals comprised within the audio stream. Further, the first electronic device 102 may be configured to analyze the one or more speech signals to detect verbal cues and inflexions (in the one or more speech signals) which may possibly indicate stress levels of the callee 114 and the one or more people near the callee 114. The first electronic device 102 may be configured to determine the emotional state of the callee 114 based on the analysis of the one or more speech signals. For example, a high pitch or tone may indicate anger or stress. A laughter in the one or more speech signals may indicate a happy emotional state, and the like.

In another example, the first electronic device 102 may be located within vicinity of the callee 114 and the callee 114 may be engaged in one or more tasks, for example, the callee 114 may be playing a musical instrument in a building. In such a case, the captured audio stream may comprise one or more ambient sounds associated with the one or more tasks with which the callee 114 is engaged. The circuitry 202 may be configured to process the captured audio stream, by use of the processor 206, to derive the one or more ambient sounds, which may be in the captured audio stream.

The circuitry 202 may be configured to analyze the derived ambient sounds to identify the environment around the callee 114, and may be further configured to thereby determine the one or more tasks with which the callee 114 is engaged. For example, in the case where the captured audio stream comprises ambient sounds indicative of guitar string strokes, then the circuitry 202 may be configured to identify the callee 114 to be in a music institute engaged in music classes. Historical data or the learned information from previous calls, (as discussed in FIG. 1) a time-of-day, and the determined communication pattern may also facilitate this identification. In such cases, the circuitry 202 may be configured to detect the user availability status of the callee 114 to be "BUSY". In accordance with an embodiment, the circuitry 202 may be configured to acquire a first location coordinate of the callee 114 from a location sensor (such as the GPS sensor 204C). The circuitry 202 may be configured to identify location of the callee 114 based on the acquired first location coordinate.

The circuitry 202 may be configured to determine the current callee-status of the callee 114 based on the determined health status of the callee 114, and the determined emotional state of the callee 114. The current callee-status may be determined further based on the determined user-availability status of the callee, the one or more tasks that the callee 114 is determined to be engaged in, and/or the acquired social media status of the callee 114.

For example, the current callee-status of the callee 114 may be one of a first callee-status, a second callee-status, and a third callee-status. The first callee-status may indicate that the callee 114 is busy with one or more tasks and may not be interested to attend the received voice call based on a current emotional state or a location (at office or at home), unless the received call is from a family member of the callee 114. The second callee-status may indicate that even though the callee 114 may be busy with the one or more tasks, the callee 114 may be interested (determined based on the health status and current emotional state) to attend to the received voice calls from family members of the callee 114 and friends of the callee 114. The third callee-status may indicate that the callee 114 may be free to attend the voice call received from the plurality of different users. The callee-status may also refer to a custom callee-status, such as "watching a movie", "Playing a Guitar", "at super-market, a "social media status", and the like, based on the analysis of content acquired from the application-based data and the plurality of sensors 204.

In certain scenarios, the circuitry 202 may be configured to redirect the received voice call to one of the third electronic device 116A and the fourth electronic device 116B via the second communication network 110 using the transceiver 210. The circuitry 202 may be configured to redirect the received voice call based on locations of the third electronic device 116A, the fourth electronic device 116B, and the callee 114. For example, locations of electronic devices (such as the third electronic device 116A and the fourth electronic device 116B) last detected in the defined physical area 118 may be stored in the memory 208. An example of storage of a last detected location of different devices in the defined physical area 118 in a personal wireless network, such as the second communication network 110, is illustrated in TABLE 3.

TABLE 3

Exemplary record of locations of electronic devices.

| Device_identifier | Device_Type | Last_Location |
|---|---|---|
| First electronic device 102 | Smartphone | Living Room |
| Third electronic device 116A | Laptop | Office Room |
| Fourth electronic device 116B | Smart watch | Living room |

Moreover, a location of the callee 114 may be determined by the circuitry 202, by use of the processor 206, based on an analysis of the application-based data. If the stored locations of the third electronic device 116A and/or the fourth electronic device 116B correspond to an area within a possible communication range of the determined location of the first electronic device 102 (location of callee 114), then the circuitry 202 may be configured to redirect the received voice call to one of the third electronic device 116A and the fourth electronic device 116B.

In accordance with an embodiment, the circuitry 202 may be configured to notify the callee 114 based on the current callee-status of the callee 114 and the level of access of the caller 112. If the current callee-status of the callee 114 is the first callee-status, then the circuitry 202 may be configured to notify the callee 114 of the received voice call exclusively if the caller 112 has the first level of access. If the current callee-status of the callee 114 corresponds to the second callee-status, then the circuitry 202 may be configured to notify the callee 114 of the received voice call if the caller 112 has the first level of access, and/or if the caller 112 has the second level of access. If the current callee-status is the third callee-status, then the circuitry 202 may be configured to notify the callee 114 of the received voice call based on a detected urgency level and/or intent (detected using speech signals in received voice call) despite the level of access assigned to the caller 112.

In accordance with an embodiment, a current caller-status of the caller 112 may be determined by the second electronic device 106 and transmitted to the first electronic device 102 via voice channels of the established voice call, as discussed in FIG. 1. The circuitry 202 may be configured to extract caller-status based audio signal from voice channels of the plurality of established voice call sessions. The first electronic device 102 may be configured to analyze the extracted caller-status-based audio signals to acquire the caller-status of the caller 112. The first electronic device 102 may be configured to determine the emotional state of the caller 112 based on the caller-status of the caller 112. Thus, the urgency level and/or intent of the caller 112 may be further verified or confirmed by the caller-status of the caller 112 extracted from the caller-status based audio signal from voice channels.

In accordance with an embodiment, the circuitry 202 may be configured to process the received speech signals to identify verbal cues and inflexions in the speech signal which may indicate a caller-status of the caller 112. The current caller-status of the caller 112 may comprise an emotional state of the caller 112. The circuitry 202 may be configured to predict the current caller-status of the caller 112 based on the analysis of the received speech signals by use of the processor 206 and the natural language processor engine 212. The circuitry 202 may be further configured to compute an urgency level associated with the caller 112 based on the predicted current caller-status and the generated contextual information associated with the caller 112. In certain scenarios, the urgency level may be one of a high urgency level, a medium urgency level and a low urgency level. For example, in the case where the generated contextual information indicates that one or more kin of the caller 112 is admitted in a hospital, and the current caller-status of the caller 112 indicates the emotional state of the caller 112 to be the tensed state, the caller 112 may be computed to have a high urgency level.

In accordance with an embodiment, the circuitry 202 may be configured to modify the level of access associated with the caller 112 based on the computed urgency level. For example, in the case where the caller 112 has the third level of access and the computed urgency level for the caller 112 is the high urgency level, the circuitry 202 may be configured to modify the level of access of the caller 112 from the third level of access to the second level of access.

In accordance with an embodiment, the circuitry 202 may be configured to process the received speech signals to extract a text query. The circuitry 202 may be configured to extract the text query by use of the processor 206 and the natural language processor engine 212, stored in the memory 208. In certain scenarios, the extracted text query may be indicative of a first data item conveyed by the caller 112 to the callee 114. In other scenarios, the extracted text query may comprise an enquiry for information from the caller 112, to the callee 114. In the case where the extracted text query is indicative of the first data item, then the circuitry 202 may be configured to further analyze the first data item and identify a data type of the first data item.

Examples of the data types of the first data may include, but are not limited to a calendar entry, a memo entry, a to-do list entry, and a note entry. Further, the first electronic device 102 may be configured to map the data type of the first data item to applications in the plurality of applications 214 stored in the first electronic device 102. For example, in the case where the first data item is the calendar entry, the circuitry 202 may be configured to map the first data item to a calendar application among the plurality of applications 214.

The circuitry 202 may be configured to modify the application-based data based on the first data item and the map of the first data item with the applications in the plurality of applications 214. For example, if the first data item is a text which reads "Hi, I am Gary! Come to my wedding on 25$^{th}$ of Apr. 2018", then the first electronic device 102 may be configured to update a calendar entry in the calendar application in the first electronic device 102 to state "Go to Gary's wedding" on a calendar column in the calendar application marked as "25$^{th}$ of Apr. 2018".

The first electronic device 102 may be configured to analyze the received signals based on the learned information from the communication pattern associated with the caller 112, and the emotional pattern associated with the caller 112. The received speech signals may be analyzed further based the application-based data, the generated contextual data associated with the caller 112, the current callee-status of the callee 114, and a relationship of the caller 112 with respect to the callee 114. The first electronic device 102 may be configured to extract the text query from the received speech signals. In certain scenarios, the extracted text query may comprise more than one data item.

In accordance with an embodiment, the first electronic device 102 may be configured to collate one or more data items in the extracted text query and the generated contextual information associated with the caller 112, to generate a gist of the extracted text query. The generated gist may be indicative of the intent of the received voice call. In accordance with an embodiment, the gist may be used by the first electronic device 102 to inform the callee 114 of the intent of the received voice call. In one example, the gist may be generated based on the extracted text query, the level of access associated with the determined identity of the caller 112, and the learned information from a plurality of voice calls received from the caller 112 over a period of time.

In another example, the gist may be generated by the call assistant application 216, based on a determined communication pattern and a determined emotional pattern associated with the determined identity of the caller 112. In certain scenarios, the gist may comprise the identity of the caller 112, the relationship of the caller 112 with respect to the callee 114, and the extracted text query, in light of the generated contextual information. The gist may be audio based, video based and/or text based. In one example, the first electronic device 102 may receive the voice call from mother of the callee 114. In the case where the callee 114 may not be available to attend the call, the call assistant application 216 may auto-answer the received voice call and establish a first voice call session. In such a case, the first electronic device 102 may determine an identity of the caller 112 associated with the received voice call.

The first electronic device 102 may process one or more speech signals received at the first electronic device 102 via the first voice call session to extract the text query. The text query extracted from the established voice call session may be a text "Please call your uncle". The first electronic device 102 may analyze the extracted text query to identify that the extracted text query is indicative of an instruction to the callee 114 to contact an uncle of the callee 114.

The first electronic device 102 may be further configured to analyze various application-based data acquired from the plurality of applications 214, to identify uncle who has been referred to by the caller 112 (mother of the callee 114). For example, the application-based data may include an Email that has the text "your only uncle, Robert Smith". In such a case, the first electronic device 102 may be configured to generate the contextual information that "Robert Smith" is the only uncle of the callee 114. The first electronic device 102 may be configured to extract information (stored in the memory 208) learned from analysis of the plurality of voice calls, received from the caller 112, over a period of time (which has been discussed in detail in FIG. 1). In one example, the first electronic device 102 may have learned from the plurality of voice calls received from the caller 112 (mother of the callee 114), over a period of time, that "Robert Smith" is sick. The first electronic device 102 may be further configured to acquire a phone number (for example, 9875441158) of "Robert Smith" from a phonebook application (stored in memory 208) of the plurality of applications 214. In such a case, the first electronic device 102 may be configured to generate a text based gist comprising words "Call Uncle Robert (Ph: 9875441158)—he is sick—regards, from your mom", in light of the generated contextual information and the learned information.

In accordance with an embodiment, the first electronic device 102 may be configured to generate a custom audio response for the received voice call based on the extracted text query, the generated gist, the determined level of access of the caller 112. The custom audio response may be generated further based on the determined current callee-status of the callee 114, the predicted current caller-status of the caller 112, and the computed urgency level of the caller 112. Moreover, the custom audio response may be generated further based on the generated contextual data of the caller 112, and the relationship of the caller 112 with respect to the callee 114. In one example, the custom audio response may comprise an artificially generated speech signal, generated by the processor 206 by use of the natural language processor engine 212, or a text-to-voice converter. The custom audio response may be generated by first electronic device 102 based on the text query extracted from the established voice call session, and based on the data type of the first data item in the extracted text query.

For example, in the case where the first data item is a calendar entry, then the circuitry 202 may update a calendar column in a calendar application based on the first data item. In such a case, the generated custom audio response may indicate "calendar has been updated, thank you for calling". The first electronic device 102 may be further configured to generate the custom audio response based on the determined communication pattern, the determined emotional pattern of the caller 112, and the generated contextual information associated with the caller 112. For example, in the case where the generated contextual information indicates that the caller 112 has low proficiency in English and has a high proficiency in Italian, the first electronic device 102 may be configured to generate the custom audio response in Italian language by use of the natural language processor engine 212 and a language converter engine stored in the memory 208. The circuitry 202 may be configured to communicate the generated custom audio response to second electronic device 106 (i.e. the caller 112) via the established voice call session.

In one exemplary aspect, the text query extracted from the received voice call may be indicative of an enquiry from the caller 112 to the callee 114. In such a case, the circuitry 202 may be configured to analyze the extracted text query and identify a question posed by the caller 112 to the callee 114. In such a case, the circuitry 202 may be configured to analyze the application-based data, by use of the processor 206, to retrieve a second data item from the application-based data, which may be used to generate an answer for the question. The circuitry 202 may be configured to extract a privacy-level assigned to the second data-item from the memory 208.

In the case where the caller 112 has a level of access (which is required to access the second data item, in light of the privacy level of the second data item), then the circuitry

202 may be configured to generate the answer to the question from the second data item, by use of the processor 206 and the natural language processor engine 212. In such a case, the circuitry 202 may be configured to generate the custom audio response based on the generated answer. The custom audio response may be communicated to the caller 112 by the circuitry 202, via the established voice call session. For example, the caller 112 may pose an enquiry to the callee 114 comprising a question, "What is your Email address?", in the established voice call session.

The circuitry 202 may be configured to analyze speech signals received via the established voice call session to extract the text query, which may comprise a question "What is your Email address". The circuitry 202 may be configured to generate the gist of the extracted text query by use of the processor 206, based on historical data (such as determined communication patterns, determined emotional patterns, and other historical data stored in the memory 208), associated with the caller 112. The circuitry 202 may be configured to determine from the generated gist that the enquiry of the caller 112 is directed towards an Email address of the callee 114. In such cases, the circuitry 202 may be configured to search the application-based data to identify an Email address associated with the callee 114.

The circuitry 202 may be configured to determine privacy level associated with the Email address from the memory 208. In the case where the first electronic device 102 identifies the Email address to have the fourth privacy level and the caller 112 to have the first level of access, the first electronic device 102 may be configured to generate an answer ("this is the desired <Email address>") to the question ("what is your Email address). The circuitry 202 may be configured to generate the custom audio response based on the generated answer. The first electronic device 102 may be further configured to communicate the custom audio response comprising the generated answer, to the caller 112, as audio response via the established voice call session in real time or near-real time.

In accordance with an embodiment, the circuitry 202 may be configured to generate a custom notification based on the custom audio response and the generated gist associated with the received voice call. The custom notification may be a light based notification, a text based notification and an audio based notification. The custom notification may be intended for the callee 114. For example, the custom notification may comprise a missed call indication from the caller 112, where the display of the missed call indication may be modified to also include the generated gist indicative of the received voice call (shown and described in FIG. 3A). In certain scenarios, the circuitry 202 may be configured to control the generated custom notification based on the extracted text query, the determined current callee-status and the predicted current caller-status.

In certain scenarios, the circuitry 202 may be configured to control the generated custom notification, by adjusting size, colour, and volume of the custom notification when the callee 114 is notified via the first electronic device 102. In accordance with an embodiment, the first electronic device 102 may be configured to present the generated custom notification on an auxiliary electronic device (such as the third electronic device 116A and/or the fourth electronic device 116B), in the case where the auxiliary electronic device is located within vicinity of the callee 114. The first electronic device 102 may be configured to communicate the generated custom notification to one of the third electronic device 116A and the fourth electronic device 116B via the second communication network 110.

In one example, the second communication network 110 may be an Internet-Of-Things (IoT) network. The generated custom notification may be presented to the callee 114 by the third electronic device 116A. If the callee 114 is absent in the defined physical area 118 in which the first electronic device 102 is located, then the first electronic device 102 may be configured to communicate the custom notification to one or more other electronic devices (such as the third electronic device 116A) via the second communication network 110 (i.e. the IoT network).

In one exemplary aspect, the circuitry 202 may be configured to interactively handle and detect multiple or different intent of the received voice call per call based on the text query (or queries) and stored historical data (such as the communication pattern and the emotional pattern) associated with the caller 112. For example, the circuitry 202 may be configured to extract multiple text queries from speech signals received via the established voice call session, based on historical data (such as determined communication patterns, determined emotional patterns, and other historical data stored in the memory 208), associated with the caller 112. For example, the circuitry 202 may be configured to extract a first text query, a second text query, and a third text query from the established voice call session. The first text query may comprise a text, "Tell Alice to bring medicines on the way home". The first electronic device 102 may have learned and stored in memory 208 that "Alice" is a first name of the callee 114. The circuitry 202 may be configured to determine from the first text query that the first text query is a query to modify a to-do list application. The circuit 202 may be configured to modify the to-do list application stored in the first electronic device 102, based on the extracted first text query. For example, the circuitry 202 may add a first custom entry with text "Bring medicines on way home" in the to-do list application. The circuitry 202 may be further configured to generate a first call response ("Okay, Alice will be reminded"). The circuitry 202 may be configured to communicate the generated first call response to the caller 112 via the established voice call session.

The second text query may comprise a text, "When will Alice be available?". The circuitry 202 may be configured to determine from the extracted second text query that the second text query is an enquiry directed towards a calendar entry of the callee 114 stored in a calendar application of the plurality of applications 214. The calendar entry may comprise information associated with availability of the callee 114 (for example, "Alice") at a certain time of day. In such cases, the circuitry 202 may be configured to search the application-based data to identify the calendar entry associated with the callee 114. The circuitry 202 may be configured to determine privacy level associated with the calendar entry from the memory 208. In the case where the first electronic device 102 identifies the calendar entry to have the fourth privacy level and the caller 112 to have the first level of access, the first electronic device 102 may be configured to generate a second call response ("Alice is available at <available time>") to the question ("When will Alice be available?"). The circuitry 202 may be configured to communicate the generated second call response to the caller 112.

The third text query may comprise a text, "We have a meeting at 11 pm tomorrow". The circuitry 202 may be configured to determine from the third text query that the third text query is a query to modify a calendar entry in a calendar application of the plurality of applications 214. The circuit 202 may be configured to modify the calendar application stored in the memory 208, based on the extracted third text query. For example, the circuitry 202 may add a second custom entry with text "YOU HAVE A MEETING AT 11:30 PM tomorrow" in the calendar application of the plurality of applications 214. The circuitry 202 may be further configured to generate a third call response ("Okay, Alice will be reminded") to the third text query ("We have a meeting at 11 pm tomorrow"). The circuitry 202 may be configured to communicate the generated third call response to the caller 112 via the established voice call session.

In one exemplary aspect, the circuitry 202 may be configured to listen in to an ongoing voice call voice call between the caller 112 and the callee 114 via the established voice call session. The circuitry 202 may be configured to analyze speech signals from the caller 112 and the callee 114 to extract multiple text queries, such as a first text query, a second text query, and a third text query.

In one example, the caller 112 may enquire the callee 114 whether the callee 114 may bring medicines to the caller 112 on way home. The callee 114 may reply in affirmative. Thereafter, the callee 114 may enquire whether the caller 112 is in possession of a contact number of a person named "Dr Gary". The caller 112 may verbally communicate the contact number of the person named "Dr Gary" to the callee 114. Thereafter, the caller 112 may verbally inform the callee 114 that the callee 114 may have to attend a meeting on a subsequent Thursday. The callee 114 may reply in affirmative for the same. In such a case, the first text query may comprise a question "Hi! can you bring medicines on your way home?". The second text query may comprise a text "Dr Gary's phone number is 987654321". The third text query may comprise a text "Thank you. Oh, by the way, we have a meeting with Robert next Thursday".

The circuitry 202 may be configured to determine from the first text query that the first text query is a query to modify a to-do list application of the plurality of applications 214. The circuitry 202 may be configured to determine from the extracted second text query that the second text query is a phone number which may be stored in a phonebook application of the plurality of applications 214. The circuitry 202 may be configured to determine from the third text query that the third text query is a query to modify a calendar entry in a calendar application of the plurality of applications 214.

The circuitry 202 may generate a set of custom notifications based on the extracted text queries. The set of custom notifications may comprise a first custom notification, a second custom notification, and a third custom notification. The first custom notification may comprise a first question ("Add item to TO DO list: "Bring medicines on your way home" ?"). The second custom notification may comprise a second question ("Add contact: "Dr. Gary (987654321)" ?"). The third custom notification may comprise a third question ("Add Calendar entry: "Meeting with Robert" on "Thursday 14 Sep. 2018" ?"). The circuitry 202 may present the set of custom notifications to the callee 114 via the first electronic device 102.

In cases where the callee 114 answers in affirmative to the first question ("Add item to TODO list: "Bring medicines on your way home" ?"), the circuit 202 may be configured to modify the to-do list application stored in the first electronic device 102, based on the extracted first text query. For example, the circuitry 202 may add a first custom entry with text "Bring medicines on way home" in the to-do list application. In cases where the callee 114 answers in affirmative to the second question (Add contact: "Dr. Gary (987654321)"?"), the circuit 202 may be configured to modify the phonebook application stored in the first electronic device 102, based on the extracted second text query. For example, the circuitry 202 may add a second custom entry with phonebook entry "Dr Gary: 987654321" in the phonebook application of the plurality of applications 214. In cases where the callee 114 answers in affirmative to the third question ("Add Calendar entry: "Meeting with Robert" on "Thursday 14 Sep. 2018" ?"), the circuit 202 may be configured to modify the calendar application stored in the memory 208, based on the extracted third text query. For example, the circuitry 202 may add a third custom entry with text "You have a meeting on Thursday, 14 Sep. 2018" in the calendar application of the plurality of applications 214. The circuitry 202 may be further configured to collate the first text query, the second text query, and the third text query to generate meeting notes. The circuitry 202 may be configured to present the generated meeting notes to the callee 114.

Figure 3A:
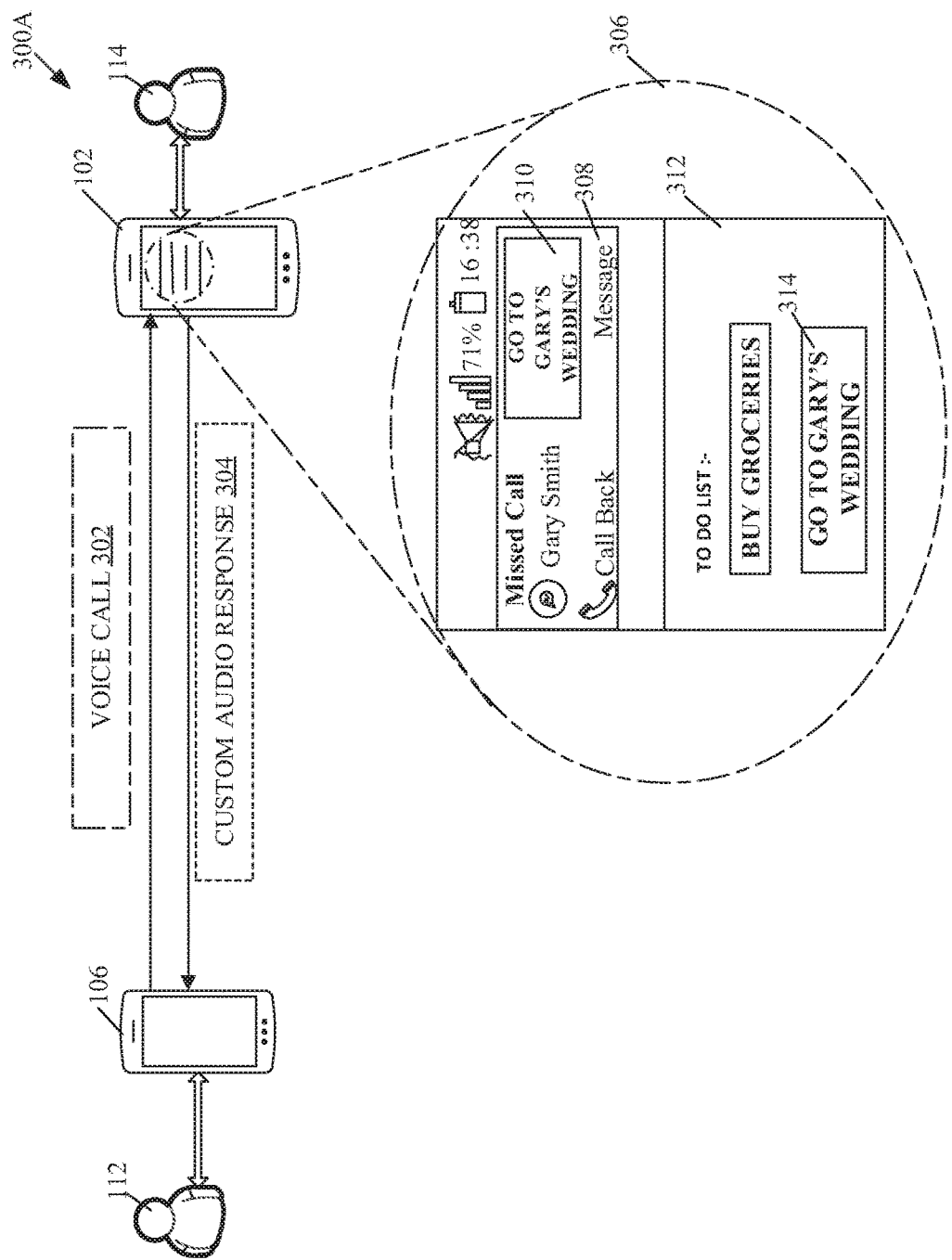
FIG. 3A to 3D illustrates exemplary scenarios for implementation of the disclosed electronic call assistant based on a callee-status and a caller-status, in accordance with an embodiment of the disclosure.

FIG. 3A illustrates an exemplary scenario for implementation of the electronic call assistant based on a current callee-status and a current caller-status, in accordance with an embodiment of the disclosure. FIG. 3A is explained in conjunction with elements from FIGS. 1 and 2. With reference to FIG. 3A, there is shown an exemplary scenario 300A. The exemplary scenario 300A may include the first electronic device 102, the second electronic device 106, the callee 114 associated with the first electronic device 102, and the caller 112 associated with the second electronic device 106.

The first electronic device 102 may receive a voice call 302 from the second electronic device 106. The first electronic device 102 may be configured to communicate a custom audio response 304 to the second electronic device 106. In accordance with the exemplary scenario 300A may further comprise a magnified view 306 of one or more dynamically customized views displayed on a display screen of the first electronic device 102. The magnified view 306 comprises an illustration of a first application card 308 (a customized view) which may be configured to present a missed call indication with additional custom notification 310 via the first electronic device 102. The first application card 308 further comprises the custom notification 310. In some embodiments, the magnified view 306 further comprises a second application card 312 that may be configured to present one or more automatically updated entries in a To-Do list application of the first electronic device 102. The second application card 312 may present a custom entry 314 in the To-do list application.

In the exemplary scenario 300A, the first electronic device 102, and the second electronic device 106 may be smartphones. The first electronic device 102 may receive the voice call 302 from the second electronic device 106. The first electronic device 102 may be configured to determine the identity of the caller 112, and the level of access associated with the determined identity, as discussed in FIG. 1. The first electronic device 102 may be configured to acquire content associated with the callee 114, (from the plurality of applications 214 and the plurality of sensors 204), based on the determined identity of the caller and a level of access associated with the determined identity. The first electronic device 102 may be configured to detect a current callee-status of the callee 114 associated with the first electronic device 102, based on the acquired content. Moreover, the first electronic device 102 may be configured to establish the voice call session and receive speech signals from the caller 112 via the established voice call session, as discussed in FIG. 1.

In accordance with an embodiment, the first electronic device 102 may be configured to process the received speech signals to extract a text query, based on historical data (such as communication pattern, emotional pattern, the application-based data, and other historical data associated with the caller 112), which may be stored in the memory 208 or the server 104. The first electronic device 102 may be configured to extract the text query based on the communication pattern associated with the caller 112, the application-based data, the generated contextual data associated with the caller 112. The first electronic device 102 may be configured to extract the text query further based on the emotional pattern associated with the caller 112, the current callee-status of the callee 114, and the relationship of the caller 112 with respect to the callee 114, as discussed in FIG. 2. In the exemplary scenario 300A, the text query may be an excerpt of the received voice call 302, such as a text, "Hi, I am Gary! Come to my wedding on 25$^{th}$ of Apr. 2018".

In the exemplary scenario 300A, the first electronic device 102 may be configured to generate a gist of the received voice call 302, based on the extracted text query, as discussed in FIG. 2. Further, the first electronic device 102 may be configured to generate the custom audio response 304 based on the generated gist of the received voice call 302. The first electronic device 102 may be further configured to generate the custom notification 310 based on the generated gist. In accordance with the exemplary scenario 300A, the first electronic device 102 may be configured to modify the display of missed call information to present the first application card 308 that includes the custom notification 310 on the first application card 308. The first electronic device 102 may be configured to modify a to-do list application stored in the first electronic device 102, based on the generated gist. For example, the first electronic device 102 may add the custom entry 314 with text "Go to gary's wedding" in the to-do list application. The first electronic device 102 may be configured to present the custom entry 314 on the second application card 312.

In the exemplary scenario 300A, the generated gist is text based (for example, "Go to gary's wedding"). As illustrated in FIG. 3A, the magnified view 306 shows the custom notification 310 that comprises a text "Go to gary's wedding" presented on the first application card 308. The magnified view 306 further comprises the custom entry 310 which may be presented in the second application card 312.

Figure 3B:
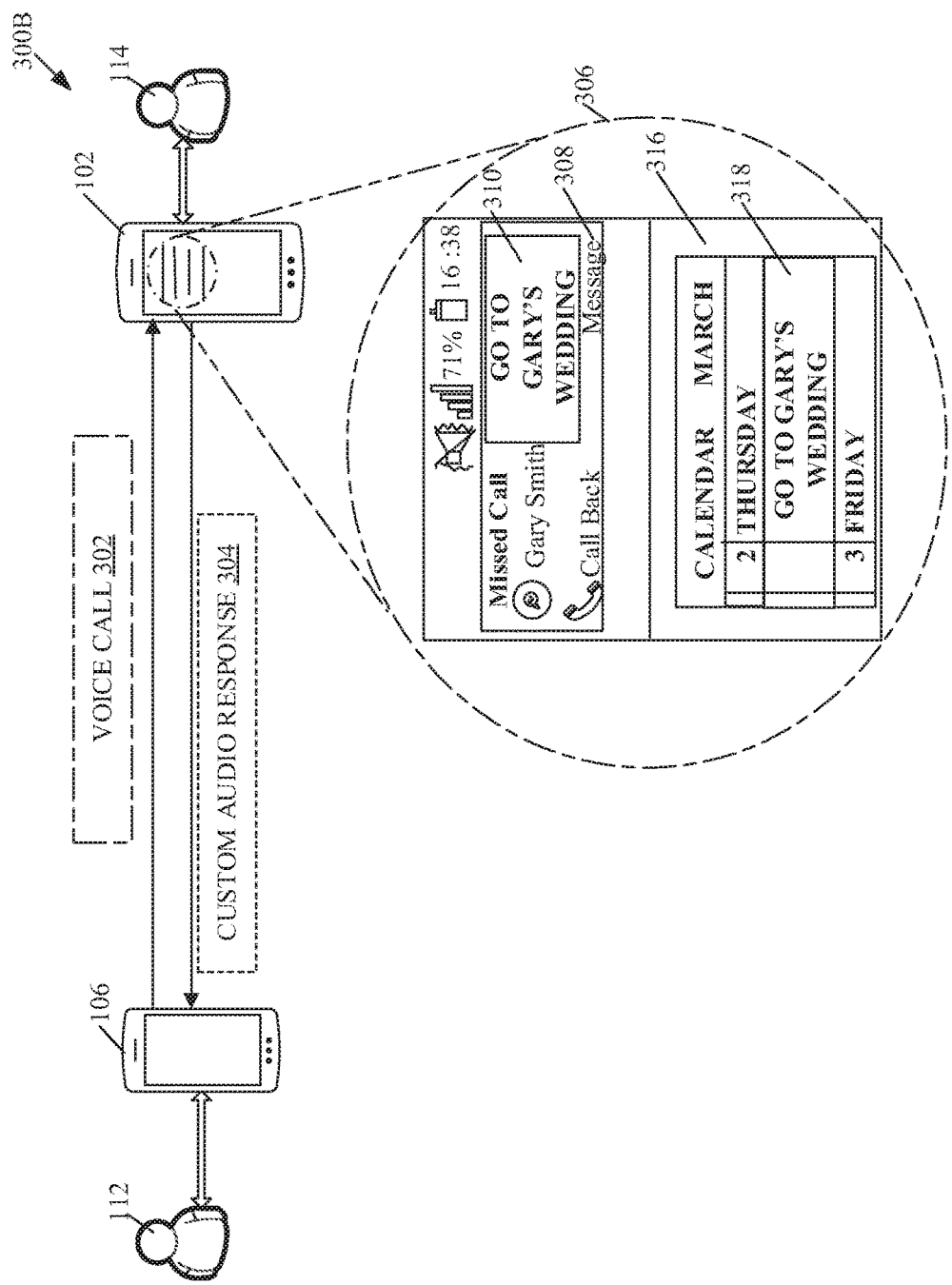

FIG. 3B illustrates an exemplary scenario 300B for implementation of the electronic call assistant based on a current callee-status and a current caller-status, in accordance with an embodiment of the disclosure. FIG. 3B is explained in conjunction with elements from FIGS. 1, 2 and 3A. With reference to FIG. 3B, there is shown an exemplary scenario 300B. The exemplary scenario 300B may be similar to that of the exemplary scenario 300A that includes the first electronic device 102, the second electronic device 106, the callee 114 associated with the first electronic device 102, and the caller 112 associated with the second electronic device 106.

In accordance with the exemplary scenario 300B may further comprise a magnified view 306 of one or more application cards displayed in a display screen of the first electronic device 102. The one or more application cards may comprise the first application card 308 and a third application card 316, which may present information (such as calendar entries) associated with a calendar application. The magnified view 306 comprises an illustration of the custom notification 310 presented on the first application card 308. Further, the magnified view 306 may comprise a custom entry 318 which may be presented on the third application card 316.

In the exemplary scenario 300B, the first electronic device 102 may receive the voice call 302 from the second electronic device 106. The first electronic device 102 may be configured to determine the identity of the caller 112, and the level of access associated with the determined identity, as discussed in FIG. 1. The call assistant application 216 installed in the first electronic device 102 may be further configured to establish the voice call session and receive speech signals from the caller 112, as discussed in FIG. 2.

In accordance with the exemplary scenario 300B, the first electronic device 102 may be configured to process the received speech signals to extract the text query. In one example, the extracted text query is, "Hi, I am Gary! Come to my wedding". In the exemplary scenario 300B, the first electronic device 102 may be configured to generate a gist of the voice call 302 based on the extracted text query, and the communication pattern and the emotional pattern associated with the caller 112, as discussed in FIG. 2. The first electronic device 102 may be further configured to generate the custom audio response 304 based on the extracted text query and/or the generated gist. The custom audio response 304 may be communicated to the second electronic device 106 of the caller 114. For example, the custom audio response may be "Your friend is currently in meeting, he will be free at 4 PM today; however, the calendar entry for the visit to Garry's wedding has been updated".

The first electronic device 102 may be configured to generate the custom notification 310 based on the generated gist, along with a missed call indication. Further, the first electronic device 102 may be configured to add the generated gist as a calendar entry to the calendar application stored in the first electronic device 102. For example, the first electronic device 102 may be configured to add the custom entry 318 into the calendar application. In the exemplary scenario 300B, the generated gist is a text "GO TO GARY'S WEDDING". As illustrated in FIG. 3B, the magnified view 306 illustrates the custom notification 310 that comprises text "GO TO GARY"S WEDDING" presented on the first application card 308, as discussed in FIG. 3A. The magnified view 306 further comprises the custom entry 318 of the calendar application, presented on the third application card 316.

Figure 3C:
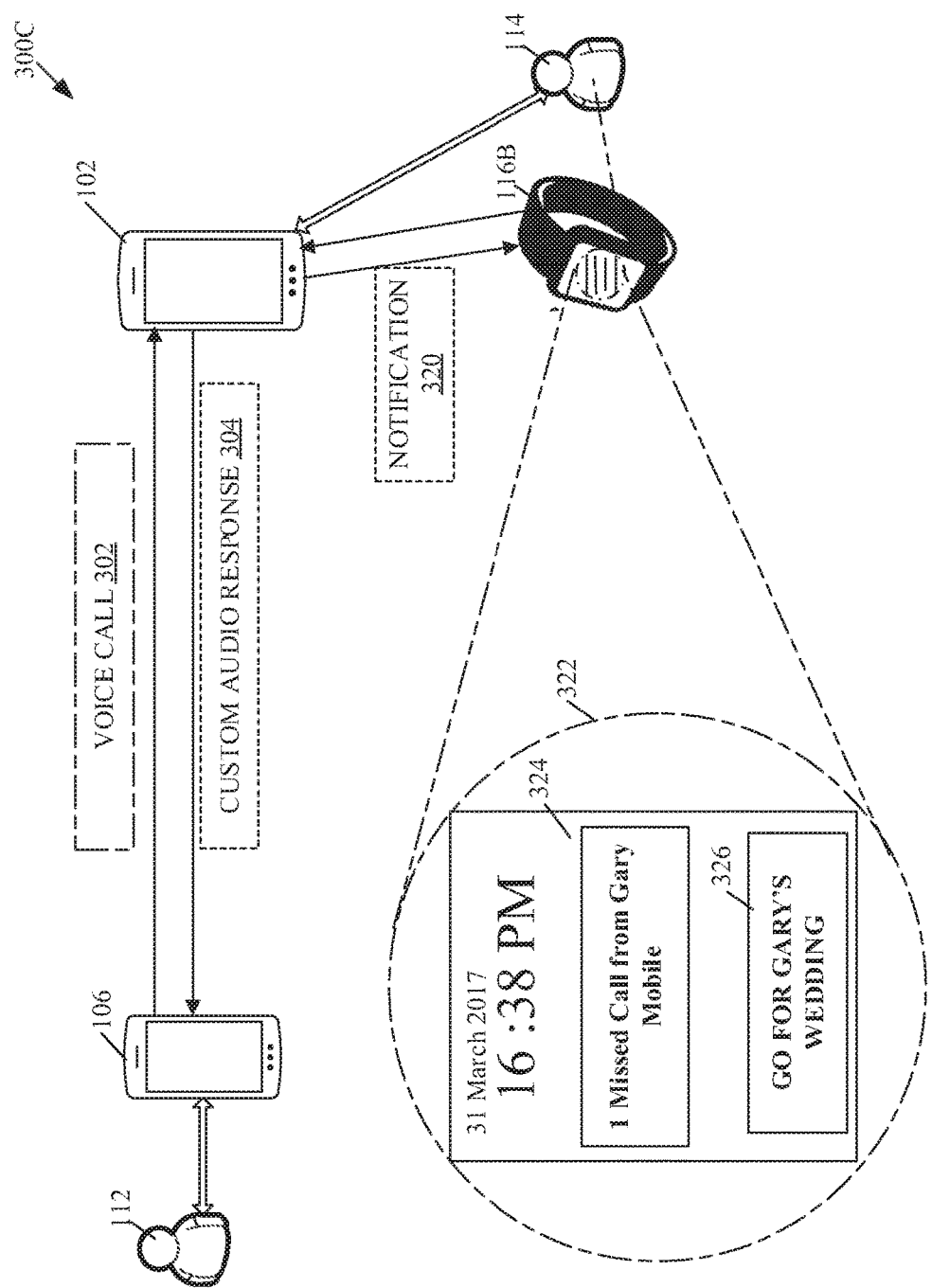

FIG. 3C illustrates an exemplary scenario 300C for implementation of the electronic call assistant based on a current callee-status and a current caller-status, in accordance with an embodiment of the disclosure. FIG. 3C is explained in conjunction with elements from FIGS. 1 and 2. With reference to FIG. 3C, there is shown an exemplary scenario 300C. The exemplary scenario 300C may include the first electronic device 102, the second electronic device 106, a fourth electronic device 116B, the callee 114 associated with the first electronic device 102 and the fourth electronic device 116B, and the caller 112 associated with the second electronic device 106. The first electronic device 102 may be configured to communicate a notification information 320 to the fourth electronic device 116B based on the received voice call 302.

In accordance with the exemplary scenario 300C, a magnified view 322 of the display screen of the fourth electronic device 116B, is shown. The magnified view 322 shows a fourth application card 324, which may present a customized missed call indication to the callee 114 on the display screen of the fourth electronic device 116B. The magnified view 322 comprises an exemplary illustration of a notification message 326, as displayed on the fourth electronic device 116B.

In the exemplary scenario 300C, the first electronic device 102 may receive the voice call 302 from the second electronic device 106. The first electronic device 102 may be configured to determine the identity of the caller 112, and the level of access associated with the determined identity, as discussed in FIG. 1. The first electronic device 102 may be further configured to establish the voice call session and receive speech signals from the caller 112, as discussed in FIG. 1.

In accordance with the exemplary scenario 300C, the first electronic device 102 may be configured to process the received speech signals to extract the text query, which may be a text, "Hi, I am Gary! Come to my wedding". The first electronic device 102 may be further configured to compute the urgency level associated with the caller 112 (which has been discussed in FIG. 2). The first electronic device 102 may be configured to detect that the callee 112 is away from the first electronic device 102 and present in vicinity of the fourth electronic device 116B.

The first electronic device 102 may be configured to generate the notification information 320 based on the extracted text query. In some embodiments, where the computed urgency level of the caller 112 is a high urgency level, the first electronic device 102 may be configured to communicate the notification information 320 to the fourth electronic device 116B. The notification information may comprise a text "GO FOR GARY's WEDDING". The notification information 320 may be used by the fourth electronic device 116B to modify display of missed call information as the fourth application card 324. Based on the modification, the fourth application card 324, (comprising the notification message 326) may be presented by the fourth electronic device 116B on the display screen of the fourth electronic device 116B.

Figure 3D:
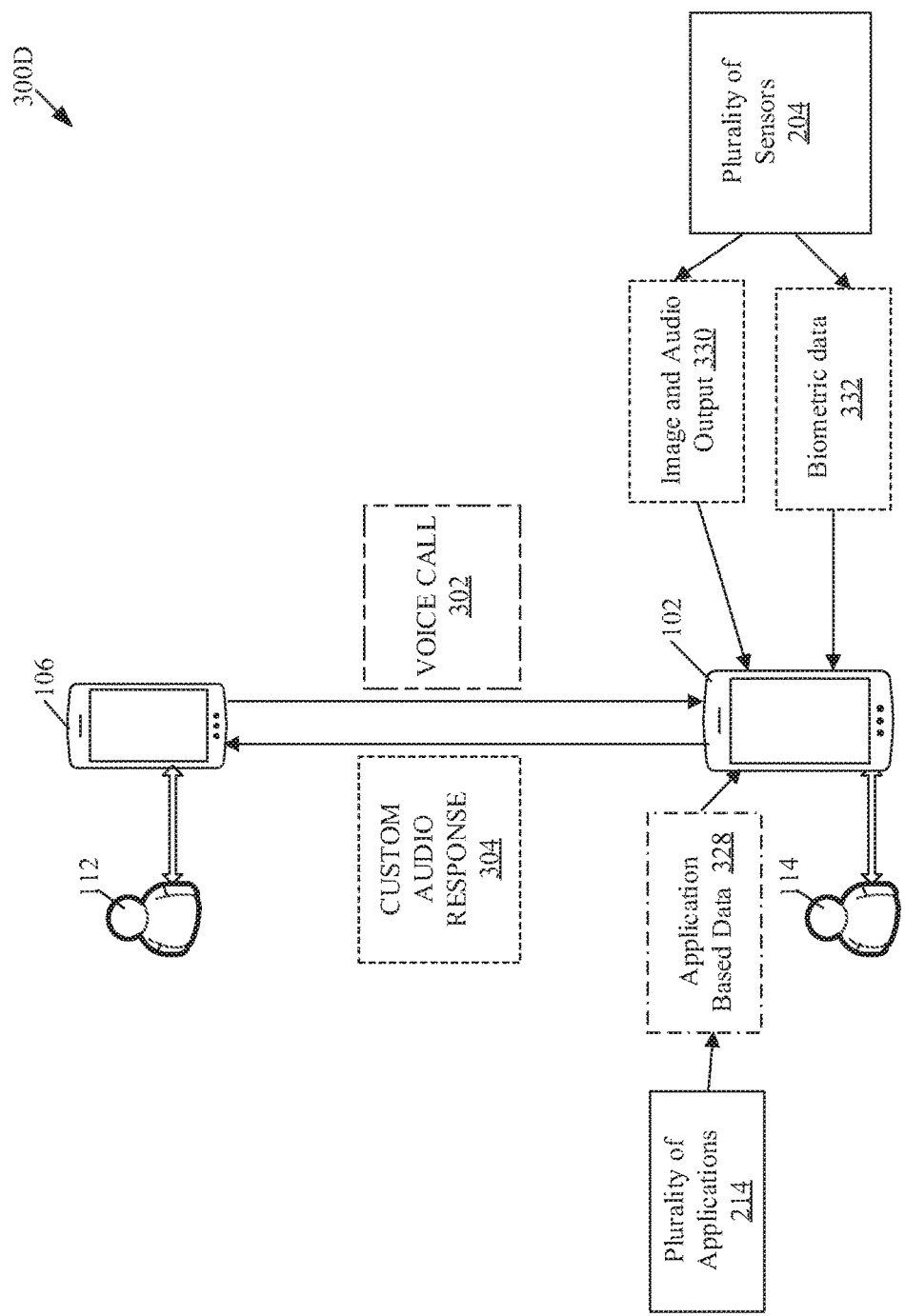

FIG. 3D illustrates an exemplary scenario 300D for implementation of the electronic call assistant based on a current callee-status and a current caller-status, in accordance with an embodiment of the disclosure. FIG. 3D is explained in conjunction with elements from FIGS. 1 and 2. With reference to FIG. 3D, there is shown an exemplary scenario 300D. The exemplary scenario 300D may include the first electronic device 102, the second electronic device 106, the callee 114 associated with the first electronic device 102 and the fourth electronic device 116B, and the caller 112 associated with the second electronic device 106. The first electronic device 102 may receive application-based data 328 extracted from the plurality of applications 214, and image and audio output 330 (such as image of the callee's face and audio streams from within vicinity of the callee) captured from the plurality of sensors 204. Further, the first electronic device 102 may process the image and audio output 330 to derive biometric data 332 associated with the callee 114 from the image and audio output 330.

In the exemplary scenario 300D, the first electronic device 102 may receive the voice call 302 from the second electronic device 106. Further, the first electronic device 102 may be configured to determine the current callee-status, the level of access associated with the caller 112, the identity of the caller 112, and the contextual information associated with the caller 112. As discussed in FIG. 2, the first electronic device 102 may determine the callee-status from the application-based data 328, the image and audio output 330, and the biometric data 332.

In accordance with the exemplary scenario 300D, the first electronic device 102 may be configured to process the received speech signals to extract the text query, which is a text, "Hi, I am Gary! Come to my wedding". In the exemplary scenario 300D, the first electronic device 102 may be configured to generate the custom audio response 304 based on the extracted text query, and one or more other parameters (such as the application-based data 328, the image and audio output 330, and the biometric data 332). The first electronic device 102 may be configured to generate the gist of the extracted text query. Based on the application-based data 328, the image and audio output 330, and the biometric data 332, the callee-status may be determined as "Sleeping now, and health status is unwell-undergoing treatment at hospital X located at <Address Y>. Further, based on the analysis of speech signals, the caller-status may be determined as "in jovial mood, presently at Home". Accordingly, the custom audio response 304 in this case based on the determined callee-status and the caller-status, may be generated, for example, as "Hi Gary, your friend <Name> is currently sleeping and unwell. Your wedding message will be visible to <Name> on display screen when he checks his phone".

Figure 4:
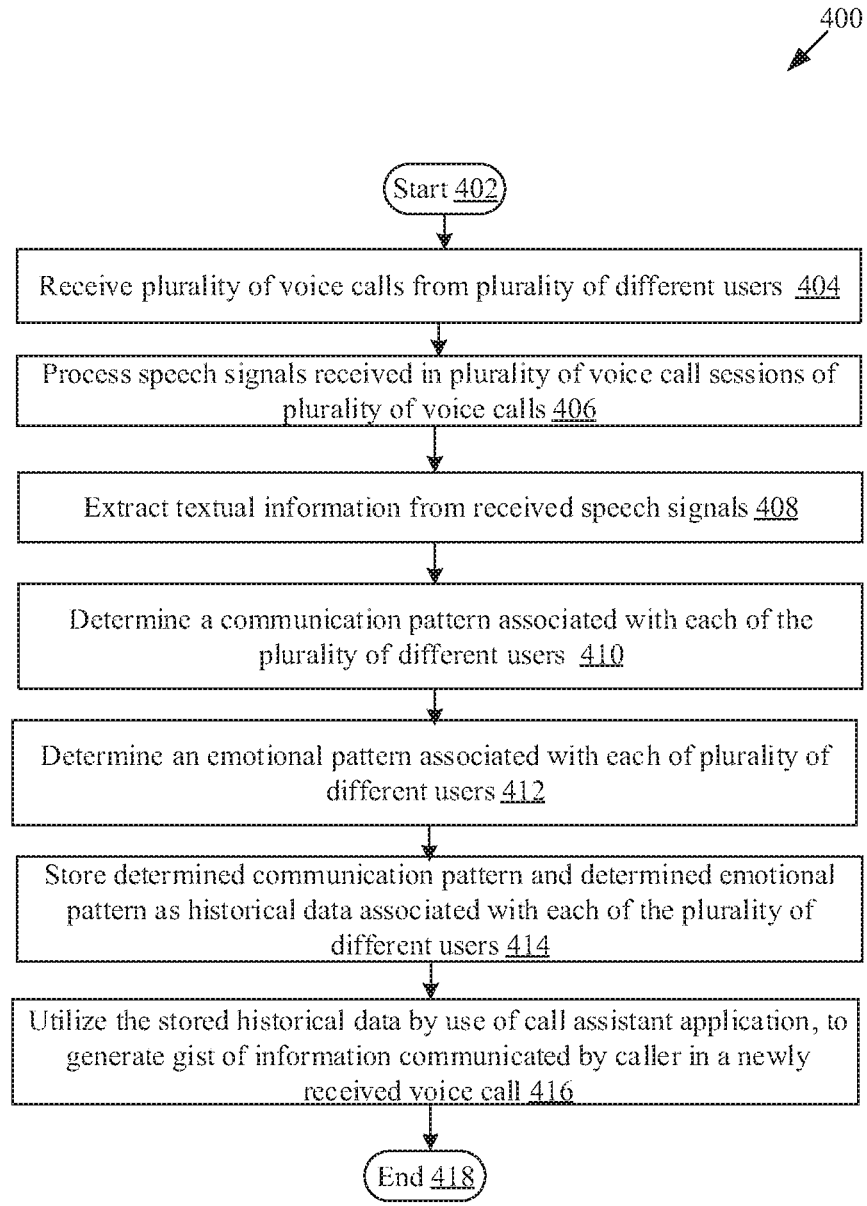
FIG. 4 depicts a first flow chart that illustrates an exemplary method for operating an electronic call assistant, in accordance with an embodiment of the disclosure.

FIG. 4 depict a flow chart that illustrates an exemplary method for operating an electronic call assistant, in accordance with an embodiment of the disclosure. With reference to FIG. 4, there is shown a flow chart 400. The flow chart is described in conjunction with FIGS. 1, and 2. The method starts at step 402 and proceeds to step 404.

At 404, the plurality of voice calls may be received by the first electronic device 102 from the plurality of different users (such as the caller 112 and other callers). The plurality of voice calls may be received by the circuitry 202 by use of the transceiver 210 via the first communication network 108. The first electronic device 102 may be configured to record and communicate the plurality of voice calls to the server 104. In some embodiments, the recorded data may not be accessible to the first electronic device 102 for privacy, and may be used exclusively for processing based on user-defined settings. The server 104 may be configured to process the plurality of voice calls to determine a communication pattern of each user of the plurality of different users. For example, the first electronic device 102 may receive a plurality of voice calls over a period of time from the same user (such as the caller 112). The first electronic device 102 may be configured to receive speech signals associated with the caller 112 during each voice call session of a plurality of voice call sessions associated with the plurality of voice calls.

At 406, the speech signals received during each of the plurality of voice call sessions of the plurality of voice calls, may be processed by the first electronic device 102. The speech signals may be processed by the circuitry 202 in the first electronic device 102 by use of the processor 206 and the natural language processor engine 212 stored in the memory 208.

At 408, textual information may be extracted from the received speech signals, by the first electronic device 102. The circuitry 202 may extract the textual information by use of the processor 206 and the natural language processor engine 212 stored in the memory 208. The textual information may indicate information communicated by each of the plurality of different users in each of the plurality of voice call sessions. The extracted textual information may be stored in the first electronic device 102 (or the server 104) as historical data.

At 410, a communication pattern associated with each of the plurality of different users, may be determined by the first electronic device 102. The circuitry 202 may be configured to determine the communication pattern associated with each of the plurality of different users, based on an analysis of the received speech signals by the processor 206. The communication pattern may include a pattern related to context or intent of a call, as discussed in FIG. 1.

At 412, an emotional pattern associated with each of the plurality of different users may be determined by the first electronic device 102. The circuitry 202 may be configured to determine the communication pattern associated with each of the plurality of different users, based on an analysis of the speech signals in the plurality of voice call sessions. The emotional patterns may comprise information with regards to temperament of the caller 112. The first electronic device 102 may classify the caller 112 as a user of one of a jovial temperament, patient temperament, short temperament, excited temperament, or neutral temperament based on the emotional pattern determined for the caller 112, as discussed in FIG. 1.

At 414, the determined communication pattern and the determined emotional pattern associated with each of the plurality of different users may be stored by the first electronic device 102 as historical data or learned information. The circuitry 202 may be configured to store the determined communication patterns and the determined emotional patterns of the plurality of different users in the memory 208.

At 416, the stored historical data (such as communication pattern, emotional pattern, and the extracted textual information), may be utilized by the call assistant application 216 (installed in the first electronic device 102) when a new call is received from the caller 112. The stored historical data may be utilized to generate a gist of information for the new call. The circuitry 202 may generate the gist by use of the processor 206, the natural language processor engine 212, and the call assistant application 216, as discussed in FIG. 1 and FIG. 2, and FIGS. 5A and 5B. The control may pass to end 418.

Figure 5A:
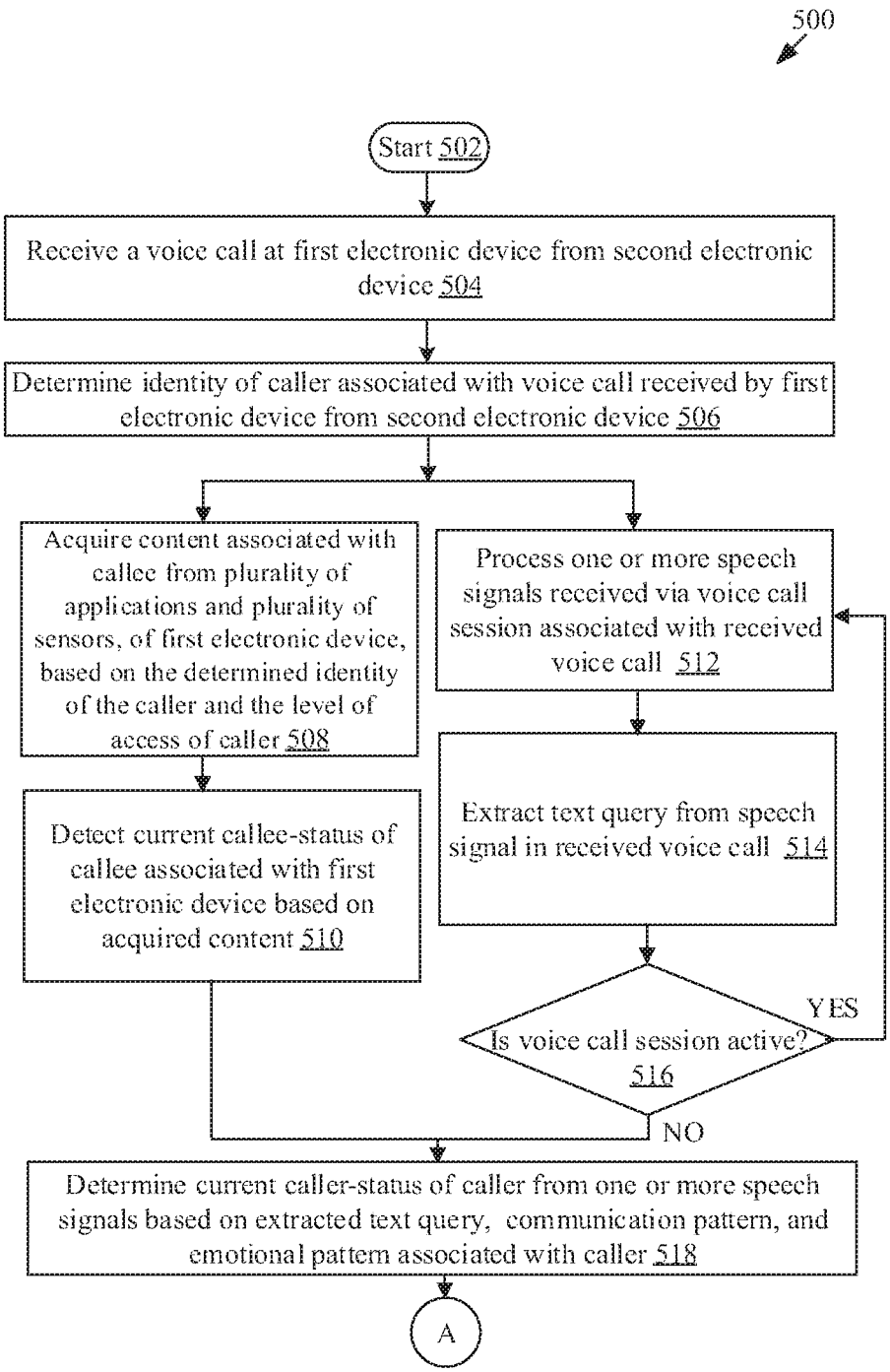
FIGS. 5A, 5B and 5C, collectively, depict a second flow chart that illustrates an exemplary method for operating an electronic call assistant, in accordance with an embodiment of the disclosure.
Figure 5B:
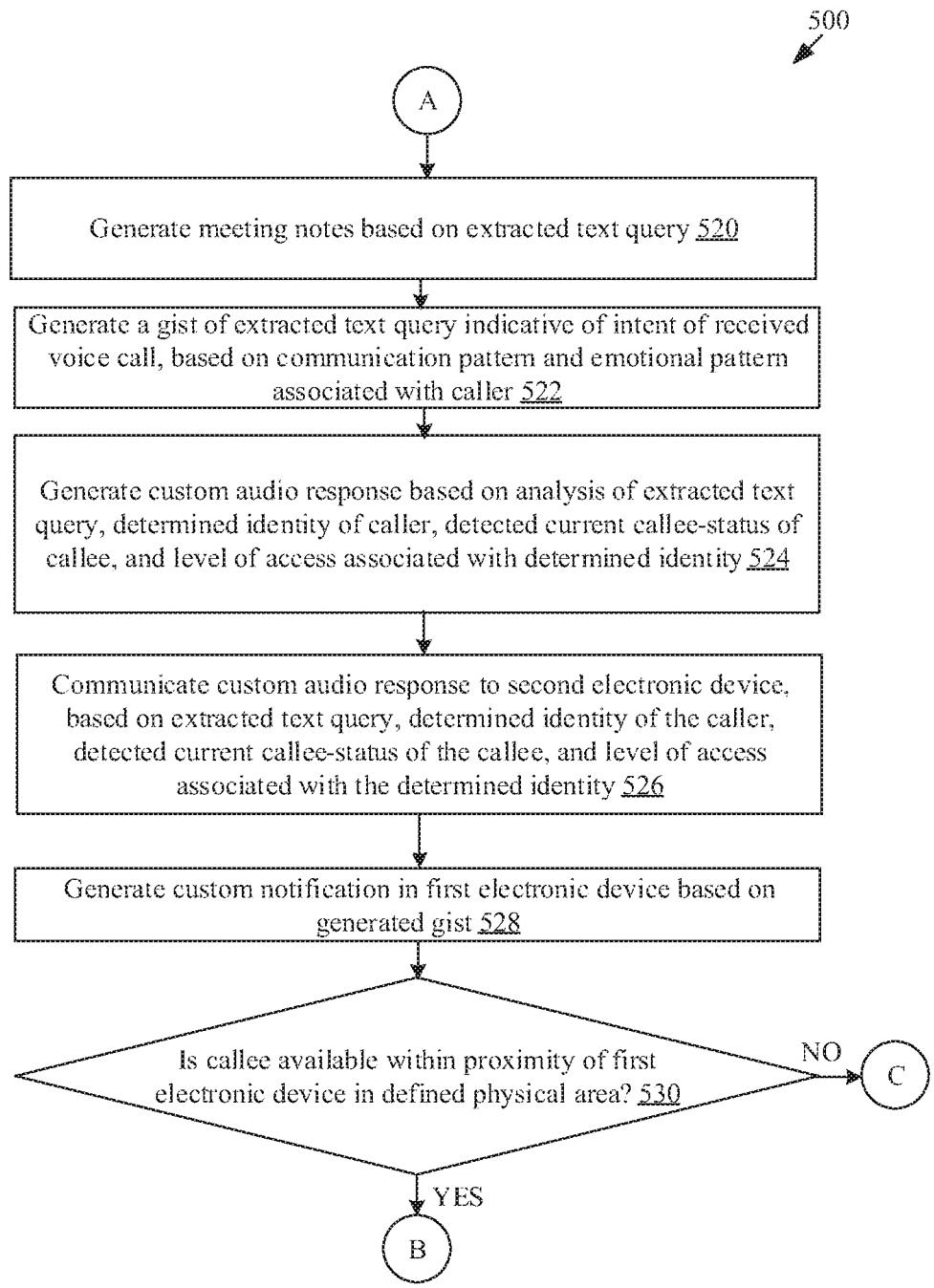
Figure 5C:
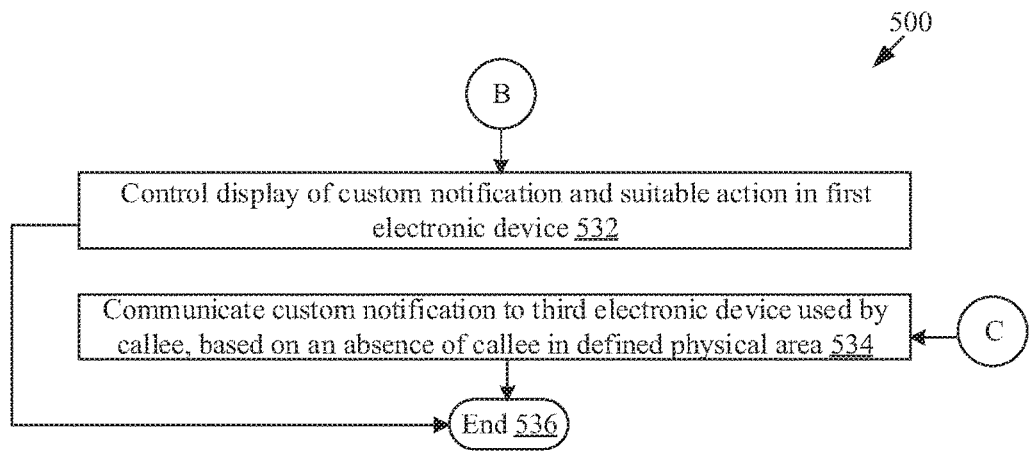

FIGS. 5A, 5B and 5C collectively depict a second flow chart that illustrates an exemplary method for operating an electronic call assistant, in accordance with an embodiment of the disclosure. With reference to FIG. 5, there is shown a flow chart 500. The flow chart is described in conjunction with FIGS. 1, 2, and 4. The method starts at step 502 and proceeds to step 504.

At 504, a voice call may be received by the first electronic device 102 (associated with the callee 114) from the second electronic device 106 (associated with the caller 112). The circuitry 202 (such as the transceiver 210) in the first electronic device 102 may be configured to receive the voice call via the first communication network 108. However, in some cases, the callee 114 may not be available to receive the received voice call. The call assistant application 216 stored in the memory 208 may be configured to establish a voice call session for the received call, in the case the callee 114 is unavailable to attend the received voice call.

At 506, identity of the caller 112 associated with the voice call received by the first electronic device 102 from the second electronic device 106, may be determined. The circuitry 202 may be configured to determine the identity of the caller 112. In certain scenarios, to determine the identity of the caller 112, the circuitry 202 may be configured to extract a phone number from the received call, via a caller identity feature associated with the received voice call, as discussed in FIG. 2. The circuitry 202 may be further configured to determine a level of access associated with the caller 112 by use of the historical data (stored in the memory 208 or the server 104) which is associated with the caller 112.

In accordance with an embodiment, the first electronic device 102 may be configured to analyze the application-based data to generate a contextual information associated with the caller 112. The contextual information may comprise information associated with the caller 112, such as a profession of the caller 112, the relationship of the caller 112 with respect to the callee 114, one or more tasks with which the caller 112 is engaged. The first electronic device 102 may be configured to modify the level of access assigned to the caller 112 based on the generated contextual information, as discussed in FIG. 2. One or more operations, such as 508, and 510 may be executed concurrently to one or more operations such as 512, 514, and 516, as shown. Therefore, the control may concurrently pass to 508 and 512.

At 508, content associated with the callee 114, may be acquired by the first electronic device 102, from the plurality of applications 214 and the plurality of sensors 204. The circuitry 202 in the first electronic device 102 may be configured to acquire the content associated with the callee, based on the determined identity of the caller, and the level of access of the caller, as discussed in FIG. 2.

At 510, the current callee-status of the callee 114 may be detected from the acquired content associated with the callee 114. The circuitry 202 in the first electronic device 102 may be configured to detect the current callee-status, from the acquired content, by use of the processor 206 and the memory 208, as discussed in FIG. 2. The current callee-status may comprise several aspects about the callee 114 such as information associated with a health status of the callee 114, an emotional state of the callee 114. The current callee-status may further comprise aspects such as a social media status of the callee 114, information associated with one or more tasks that the callee 114 may be engaged in a user-availability status of the callee 114, or a combination thereof. The circuitry 202 may be configured to detect the current callee-status of the callee 114 based on the health status of the callee 114, and the emotional state of the callee 114. The current callee-status may be determined further based on the determined user-availability status of the callee, the one or more tasks that the callee 114 is determined to be engaged in, and/or the acquired social media status of the callee 114.

At 512, one or more speech signals received via the established voice call session (associated with the received voice call), may be processed by the first electronic device 102. The circuitry 202 in the first electronic device 102 may be configured to process the one or more speech signals by use of the processor 206 and the natural language processor engine 212.

At 514, a text query may be extracted by the first electronic device 102, from the received speech signals. In certain scenarios, the circuitry 202 may be configured to extract the text query by use of stored historical data (such as communication pattern) which is associated with the caller 112. In other scenarios, the server 104 may be configured to extract the text query by use of stored historical data (such as communication pattern) which is associated with the caller 112. In one embodiment, the circuitry 202 may be configured to extract the text query by use of the processor 206, the voice-to-text converter, and the natural language processor engine 212 stored in the memory 208. In other embodiments, the text query may be extracted from the received one or more speech signals, by the server 104.

At 516, it may be checked if the voice call session is active. The circuitry 202 may be configured to check that the established voice call session is active or not. In the case where the established voice call session is active, the control may pass to 512. In the case where the established voice call session is inactive or terminated, the control may pass to

518. In cases where the established voice call session is active for a certain time period, the circuitry 202 may be configured to perform one or more operations such as 512, 514, and 516 recursively until the established voice call session may be terminated. In such scenarios, control may pass to 514 repeatedly and the circuitry 202 may extract a plurality of text queries by analyzing speech signals received from the established voice call session. The first electronic device 102 may be configured to analyze the plurality of extracted text queries to determine a suitable action which may be subsequently performed by the first electronic device based on the plurality of extracted text queries. Examples of the determined suitable action may include, but is not limited to a first action to update a reminder application of the plurality of applications 214, a second action to update a calendar application of the plurality of applications 214, a third action to update a phonebook application of the plurality of applications 214, and other actions.

At 518, a current caller-status of the caller 112 may be determined by the first electronic device 102 from the received one or more speech signals. The circuitry 202 may be configured to process the received one or more speech signals based on the communication pattern and the emotional pattern associated with the caller 112, to determine the current caller-status, as discussed in FIG. 2. In one example, the circuitry 202 may be configured to process the received speech signals to identify verbal cues and inflexions in the received speech signal, which may indicate the current-caller-status of the caller 112, as discussed in FIG. 2. In some embodiments, the circuitry 202 may process the application-based data from the plurality of applications 214 to generate contextual information associated with the caller 112, and thereby detect the current caller-status, as discussed in FIG. 2.

At 520, meeting notes may be generated based on the extracted text query and stored historical data (such as the communication pattern and the emotional pattern) associated with the caller 112. The circuitry 202 (such as the processor 206) may be configured to generate the meeting notes by use of the call assistant application 216. In accordance with an embodiment, the meeting notes may be presented to the callee 114 by the first electronic device 102 to inform the callee 114 of the received voice call. In one example, the first electronic device 102 may be configured to collate the plurality of extracted text queries to generate meeting notes of the received voice call. The generated meeting notes may be stored by the circuitry 202, in the memory 208, for future reference. The circuitry 202 may be further configured to generate a summary of the generated meeting notes. The generated summary may further comprise information associated with the callee 114. Information associated with the callee 114 may comprise the determined current-callee-status.

At 522, a gist indicative of an intent of the received voice call may be generated by the first electronic device 102 based on the extracted text query and stored historical data (such as the communication pattern and the emotional pattern) associated with the caller 112. The circuitry 202 (such as the processor 206) may be configured to generate the gist by use of the call assistant application 216. In accordance with an embodiment, the gist may be used by the first electronic device 102 to inform the callee 114 of the intent of the received voice call. In accordance with an embodiment, the first electronic device 102 may be configured to collate one or more data items in the extracted text query and the generated contextual information associated with the caller 112, to generate a gist of the extracted text query.

At 524, a custom audio response for the received voice call may be generated by the first electronic device 102, based on an analysis of the extracted text query, the determined identity of the caller 112, the detected current callee-status of the callee, and the determined level of access of the caller 112. The circuitry 202 may be configured to analyze the extracted text query by use of the processor 206, and the natural language processor engine 212. The custom audio response may be generated based on the detected current callee-status of the callee 114, and the determined current caller-status of the caller 112. In one example, the custom audio response may comprise an artificially generated speech signal, generated by the processor 206, a text-to-voice converter, and the natural language processor engine 212. Examples of the custom audio response, such as the custom audio response 304, is shown and described in FIGS. 3A to 3D.

At 526, the generated custom audio response may be communicated to the second electronic device 106 based on the extracted text query, the determined identity of the caller, the detected current callee-status of the callee, and the level of access associated with the determined identity of the caller 112. The circuitry 202 may be configured to communicate the generated custom audio response to the second electronic device 106 by use of the transceiver 210, via the first communication network 108.

At 528, a custom notification may be generated by the first electronic device 102 based on the custom audio response and the generated gist associated with the received voice call. The circuitry 202 may be configured to generate the custom notification by use of the processor 206, the natural language processor engine 212, and the call assistant application 216. In one embodiment, the custom notification may comprise a missed call indication from the caller 112 along with the generated gist indicative of the received voice call.

At 530, availability (or presence) of the callee 114 within proximity of the first electronic device 102 in the defined physical area 118 may be checked by the first electronic device 102. The circuitry 202 may check the availability of the callee 114 in the defined physical area 118 by use of the processor 206, the GPS sensor 204C and the acquired content. In the case where the callee 114 is present within the defined physical area, within proximity of the first electronic device 102, the control may pass to 532. In cases where the callee 114 is absent from the defined physical area, the control may pass to 534. In certain scenarios, the circuitry 202 may extract location (stored in the memory 208, as discussed in FIG. 2) of one or more electronic devices (such as the third electronic device 116A and the fourth electronic device 116B) used by the callee 114.

At 532, display of the generated custom notification and a suitable action in the first electronic device 102 may be controlled. The circuitry 202 may control the display of the custom notification by adjusting size, colour, and volume of the custom notification when the callee 114 is notified via the first electronic device 102. The circuitry 202 may control the suitable action in the first electronic device 102. For example, the circuitry 202 may update a calendar application of the plurality of applications 214 stored in the first electronic device 102, based on the plurality of extracted text queries.

At 534, the custom notification may be transmitted from the first electronic device 102 to the one or more electronic devices (such as the third electronic device 116A) used by the callee 114, based on an absence of the callee in a defined physical area in which the first electronic device 102 is located. In accordance with an embodiment, the first electronic device 102 may be configured to present the generated custom notification on the third electronic device 116A. In one embodiment, the first electronic device 102 may be configured to communicate the generated custom notification to one of the the third electronic device 116A and the fourth electronic device 116B via the second communication network 110. The control may pass to end 536.

In accordance with an embodiment of the disclosure, an electronic call assistant based on a caller-status and a callee-status is disclosed. The electronic call assistant may be implemented in a first electronic device (such as the first electronic device 102 (FIG. 1)). The first electronic device 102 may comprise one or more sensors (such as the plurality of sensors 204 (FIG. 2)), a memory (such as the memory 208 (FIG. 2)), and a circuitry (such as the circuitry 202 (FIG. 2)). The memory 208 in the first electronic device 102 may be configured to store a plurality of applications (such as the plurality of applications 214 (FIG. 2)). The circuitry 202 in the first electronic device 102 may be configured to determine an identity of a caller (such as the caller 112 (FIG. 1)) of a voice call (e.g. the voice call 302 (FIG. 3A, FIG. 3B, FIG. 3C, and FIG. 3D)) received by the first electronic device 102 from a second electronic device (such as the second electronic device 106 (FIG. 1)).

The circuitry 202 may be configured to acquire content from the plurality of applications 214 and the one or more sensors of the first electronic device 102, based on the determined identity of the caller 112 and a level of access associated with the determined identity. The circuitry 202 may be further configured to detect a current callee-status of a callee (such as the callee 114 (FIG. 1)) associated with the first electronic device 102 based on the acquired content. The circuitry 202 may be configured to extract a text query from a speech signal in the received voice call. The circuitry 202 may be further configured to communicate a custom audio response (e.g. the custom audio response 304 (FIG. 3A, FIG. 3B, FIG. 3C, and FIG. 3D)), to the second electronic device 106 based on the extracted text query, the determined identity of the caller 112, the detected current callee-status of the callee 114, and the level of access associated with the determined identity.

Various embodiments of the disclosure may provide a non-transitory computer readable medium and/or storage medium having stored thereon, a set of instructions executable by a machine and/or a computer to operate an electronic call assistant based on a callee-status and a caller-status. The set of instructions may cause the machine and/or computer to perform operations that comprise storage of a plurality of applications in a memory. The operations may further comprise determination of an identity of a caller of a voice call received by the first electronic device from a second electronic device, acquisition of content from the plurality of applications and the one or more sensors of the first electronic device. The content may be acquired based on the determined identity of the caller and a level of access associated with the determined identity. The operations may further comprise detection of a current callee-status of a callee associated with the first electronic device based on the acquired content, extraction of a text query from a speech signal in the received voice call, communication of a custom audio response to the second electronic device. The custom audio response may be communicated based on the extracted text query, the determined identity of the caller, the detected current callee-status of the callee, and the level of access associated with the determined identity.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted to carry out the methods described herein may be suited. A combination of hardware and software may be a general-purpose computer system with a computer program that, when loaded and executed, may control the computer system such that it carries out the methods described herein. The present disclosure may be realized in hardware that comprises a portion of an integrated circuit that also performs other functions.

The present disclosure may also be embedded in a computer program product, which comprises all the features that enable the implementation of the methods described herein, and which, when loaded in a computer system, is able to carry out these methods. Computer program, in the present context, means any expression, in any language, code or notation, of a set of instructions intended to cause a system with an information processing capability to perform a particular function either directly, or after either or both of the following: a) conversion to another language, code or notation; b) reproduction in a different material form.

While the present disclosure has been described with reference to certain embodiments, it will be understood by those skilled in the art that various changes may be made and equivalents may be substituted without deviation from the scope of the present disclosure. In addition, many modifications may be made to adapt a particular situation or material to the teachings of the present disclosure without deviation from its scope. Therefore, it is intended that the present disclosure not be limited to the particular embodiment disclosed, but that the present disclosure will include all embodiments falling within the scope of the appended claims.

What is claimed is:

1. An electronic call assistant system, comprising:
   at least one sensor in a first electronic device;
   a memory, in the first electronic device, configured to store a plurality of applications; and
   circuitry, in the first electronic device, configured to:
   determine an identity of a caller of a voice call received by the first electronic device from a second electronic device;
   acquire content from the plurality of applications and the at least one sensor of the first electronic device, based on the determined identity of the caller and a level of access associated with the determined identity of the caller;
   determine a current callee-status of a callee associated with the first electronic device based on the acquired content;
   extract a text query from a speech signal in the received voice call;
   determine a current caller-status of the caller associated with the second electronic device based on a voice stress level of the speech signal in the received voice call;
   allow, for the caller, access to the content, based on the level of access associated with the determined identity of the caller and a privacy level associated with an application of the plurality of applications, wherein the privacy level is indicative of confirmation of the callee that the application of the plurality of applications is a user-analyzable application;

communicate a custom audio response to the second electronic device based on the extracted text query, the determined identity of the caller, the determined current callee-status of the callee, the determined current caller-status of the caller, and the level of access associated with the determined identity; and generate a gist indicative of an intent of the received voice call based on the extracted text query, the level of access associated with the determined identity of the caller, and learned information from a plurality of voice calls previously received by the first electronic device from the caller.

2. The electronic call assistant system according to claim 1, wherein the current callee-status of the callee corresponds to at least one of an emotional status of the callee, a health status of the callee, a social media status of the callee, or a user availability status.

3. The electronic call assistant system according to claim 1, wherein the circuitry is further configured to:
acquire the current caller-status of the caller based on metadata in the speech signal in the received voice call, and
wherein the metadata is embedded by the second electronic device in the received voice call as an inaudible signal that is inaudible to the callee.

4. The electronic call assistant system according to claim 1, wherein the circuitry is further configured to establish a voice call session between the second electronic device of the caller and the first electronic device of the callee, and
wherein the custom audio response is communicated in the established voice call session.

5. The electronic call assistant system according to claim 1, wherein the circuitry is further configured to capture at least one of an image or voice of the callee by the at least one sensor for the determination of the current callee-status of the callee.

6. The electronic call assistant system according to claim 1, wherein the circuitry is further configured to determine the current caller-status of the caller associated with the second electronic device based on the extracted text query.

7. The electronic call assistant system according to claim 6, wherein the circuitry is further configured to determine an urgency level for the caller to communicate with the callee based on the determined current caller-status of the caller.

8. The electronic call assistant system according to claim 7, wherein the circuitry is further configured to modify the level of access associated with the determined identity based on the determined urgency level for the caller to communicate with the callee.

9. The electronic call assistant system according to claim 1, wherein the circuitry is further configured to:
detect a third electronic device currently associated with the callee; and re-direct information received from the first electronic device to the detected third electronic device of the callee, via a personal wireless network,
wherein the received information from the first electronic device corresponds to at least one of the voice call, a text message, or a custom notification.

10. The electronic call assistant system according to claim 1, wherein the circuitry is further configured to generate the custom audio response based on an analysis of the extracted text query, the determined identity of the caller, the determined current callee-status of the callee, and the level of access associated with the determined identity.

11. The electronic call assistant system according to claim 1, wherein the circuitry is further configured to identify a relationship of the caller with respect to the callee based on the determined identity of the caller.

12. The electronic call assistant system according to claim 1, wherein the circuitry is further configured to determine a communication pattern and an emotional pattern of the caller based on historical data extracted from the plurality of voice calls previously received by the first electronic device from the second electronic device of the caller.

13. The electronic call assistant system according to claim 1, wherein the circuitry is further configured to control display of a custom notification at the first electronic device, and
wherein the custom notification comprises a missed call indication from the caller along with the gist indicative of the intent of the received voice call.

14. The electronic call assistant system according to claim 13, wherein the circuitry is further configured to communicate the custom notification from the first electronic device to a third electronic device currently associated with the callee, based on an absence of the callee in a defined physical area in which the first electronic device is located.

15. A method, comprising:
in a first electronic device comprising a memory and circuitry,
storing, by the circuitry, a plurality of applications in the memory;
determining, by the circuitry, an identity of a caller of a voice call received at the first electronic device from a second electronic device;
acquiring, by the circuitry, content from the plurality of applications and from at least one sensor of the first electronic device, based on the determined identity of the caller and a level of access associated with the determined identity of the caller;
determining, by the circuitry, a current callee-status of a callee associated with the first electronic device based on the acquired content;
extracting, by the circuitry, a text query from a speech signal in the received voice call;
allowing, for the caller, access to the content, based on the level of access associated with the determined identity of the caller and a privacy level associated with an application of the plurality of applications, wherein the privacy level is indicative of confirmation of the callee that the application of the plurality of applications is a user-analyzable application;

communicating, by the circuitry, a custom audio response to the second electronic device based on the extracted text query, the determined identity of the caller, the determined current callee-status of the callee, a determined current caller-status of the caller, and the level of access associated with the determined identity; and generating, by the circuitry, a gist indicative of an intent of the received voice call based on the extracted text query, the level of access associated with the determined identity of the caller, and learned information from a plurality of voice calls previously received by the first electronic device from the caller.

16. The method according to claim 15, wherein the current callee-status of the callee corresponds to at least one of an emotional status, a health status, a social media status, or a user availability status.

17. The method according to claim 15, further comprising establishing, by the circuitry, a voice call session between the second electronic device of the caller and the first electronic device of the callee, wherein the custom audio response is communicated in the established voice call session.

18. The method according to claim 15, further comprising capturing, by the circuitry, at least one of an image, voice, or health parameters of the callee by the at least one sensor for the determination of the current callee-status of the callee.

19. The method according to claim 15, further comprising controlling, by the circuitry, display of a custom notification at the first electronic device, wherein the custom notification comprises a missed call indication for the voice call from the caller along with the gist indicative of the intent of the received voice call.

20. The method according to claim 19, further comprising communicating, by the circuitry, the custom notification from the first electronic device to a third electronic device currently associated with the callee, based on an absence of the callee in a defined physical area in which the first electronic device is located.

* * * * *